US006690817B1

(12) United States Patent
Cabib et al.

(10) Patent No.: US 6,690,817 B1
(45) Date of Patent: Feb. 10, 2004

(54) SPECTRAL BIO-IMAGING DATA FOR CELL CLASSIFICATION USING INTERNAL REFERENCE

(75) Inventors: Dario Cabib, Timrat (IL); Robert A. Buckwald, Ramat Yishai (IL); Nissim Ben-Yosef, Jerusalem (IL)

(73) Assignee: Applied Spectral Imaging Ltd., Migdal Haemek (IL)

( * ) Notice: Subject to any disclaimer, the term of this patent is extended or adjusted under 35 U.S.C. 154(b) by 0 days.

(21) Appl. No.: 09/157,138

(22) Filed: Sep. 18, 1998

Related U.S. Application Data

(63) Continuation-in-part of application No. 08/824,234, filed on Mar. 25, 1997, now Pat. No. 5,991,028, which is a continuation-in-part of application No. 08/571,047, filed on Dec. 12, 1995, now Pat. No. 5,784,162, which is a continuation-in-part of application No. 08/392,019, filed on Feb. 21, 1995, now Pat. No. 5,539,517, which is a continuation-in-part of application No. 08/107,673, filed on Aug. 18, 1993, now abandoned.

(51) Int. Cl.$^7$ .................................................. G06K 9/62
(52) U.S. Cl. ...................... 382/134; 382/165; 382/224
(58) Field of Search ................................. 382/133, 134, 382/164–165, 167, 224, 225; 702/21; 435/7.23, 7.24, 7.25, 6; 356/346

(56) References Cited

U.S. PATENT DOCUMENTS

| | | | | |
|---|---|---|---|---|
| 3,873,974 A | * | 3/1975 | Bouton et al. | 382/134 |
| 4,207,554 A | * | 6/1980 | Resnick et al. | 382/133 |
| 4,850,024 A | * | 7/1989 | Motoike et al. | 382/134 |
| 5,016,283 A | * | 5/1991 | Bacus et al. | 382/133 |
| 5,335,293 A | * | 8/1994 | Vannelli et al. | 382/165 |
| 5,539,517 A | * | 7/1996 | Cabib et al. | 356/346 |
| 5,568,400 A | * | 10/1996 | Stark et al. | 702/85 |
| 5,605,805 A | * | 2/1997 | Verwer et al. | 382/134 |
| 5,732,150 A | | 3/1998 | Zhou et al. | 382/133 |
| 5,834,203 A | * | 11/1998 | Katzir et al. | 435/6 |

OTHER PUBLICATIONS

Cabib et al. "Spatially resolved Fourier Transform Spectroscopy (Spectral Imaging): a powerful tool for quantitative analytical microscopy," Proc. of SPIE, vol. 2678, pp. 278–291, Jan. 1996.*
Garini et al. "Spectral Karyotyping." *Bioimaging*, vol. 4, pp. 65–72, Jan. 1996.*
Malik et al. "Fourier Transform Multipixel Spectroscopy for Quantitative Cytology," *Journal of Microscopy*, vol. 182, pt. 2, pp. 133–140, May 1996.*
Soenksen et al. "Multicolor FISH Using a Novel Spectral Bioimaging Sytem," Proceedings of SPIE, vol. 2678, pp. 303–309, Feb. 1996.*

* cited by examiner

*Primary Examiner*—Jon Chang
(74) *Attorney, Agent, or Firm*—G. E. Ehrlich (1995) Ltd.

(57) ABSTRACT

A method of spectral-morphometric analysis of biological samples, the biological samples including substantially constant components and suspected variable components, the method is effected by following the steps of (a) using a spectral data collection device for collecting spectral data of picture elements of the biological samples; (b) defining a spectral vector associated with picture elements representing a constant component of at least one of the biological samples; (c) using the spectral vector for defining a correcting function being selected such that when operated on spectral vectors associated with picture elements representing other constant components, spectral vectors of the other constant components are modified to substantially resemble the spectral vector; (d) operating the correcting function on spectral vectors associated with at least the variable components for obtaining corrected spectral vectors thereof; and (e) classifying the corrected spectral vectors into classification groups.

22 Claims, 8 Drawing Sheets

(5 of 8 Drawing Sheet(s) Filed in Color)

The normal group

The ALL group

ALL 113  ALL 212  ALL 218

The CLL group

CLL 97

The IM group

Before Correction

After Correction

IM 10  IM 11

The PCL group

Before Correction

After Correction

PCL 10  PCL 28

The PLL group

Before Correction

After Correction

PLL 11    PLL 24

The Sezary group

Before Correction

After Correction

Sezary 20    Sezary 24

SPECTRAL BIO-IMAGING DATA FOR CELL CLASSIFICATION USING INTERNAL REFERENCE

This is a continuation-in-part of U.S. patent application Ser. No. 08/824,234, filed Mar. 25, 1997, now U.S. Pat. No. 5,991,028 which is a continuation-in-part of U.S. patent application Ser. No. 08/571,047, filed Dec. 12, 1995, now U.S. Pat. No. 5,784,162, issued Jul. 21, 1998, which is a continuation-in-part of U.S. patent application Ser. No. 08/392,019 filed Feb. 21, 1995, now U.S. Pat. No. 5,539,517, issued Jul. 23, 1996, which is a continuation-in-part of U.S. patent application Ser. No. 08/107,673, filed Aug. 18, 1993, now abandoned.

FIELD AND BACKGROUND OF THE INVENTION

The present invention relates to spectral methods in general and, more particularly, to spectral imaging methods for cell classification, biological research, medical diagnostics and therapy, which methods are referred to hereinbelow as spectral bio-imaging methods. The spectral bio-imaging methods of the present invention can be used to provide automatic and/or semiautomatic spectrally resolved morphometric classification (e.g., detection, grading) of neoplasm, by standardizing the measured spectra of biological material present in biological samples in general, but more specifically when these samples are stained for microscopy imaging, and as a result enabling the building of libraries of spectral signatures for these biological objects, and therefore allowing automatic and semiautomatic analysis of such samples. Also, cytological or tissue section specimen which are generally stained with chromogenic dyes, simultaneously with, or without, specific tagged or marked expressed proteins and/or genes and/or DNA segments, to be measured by bright field light microscopy have the advantages over fluorescently dyed, tagged and/or marked specimen, of being significantly more permanent and therefore of providing means to repeat the tests at later times, of avoiding the background signals due to auto fluorescence of the specimen itself, and in general of being less expensive, at least at present. By helping overcome the signal variations due to drifts in staining colors and concentrations, due to different manufacturing processes of the stains, different origins of the stains, and other environmental reasons, and instabilities of the measuring instrumentation, due to drifts in the illumination spectrum and/or intensity, changes in the optics spectral transmission, and spectral response of the detector array, the methods can be used for the improvement and automatization of the detection of the spatial organization and of the qualification and quantification of cellular and tissue constituents and structures associated with, for example, tumorogenesis, using, for example, light transmission microscopy combined with high spatial and spectral resolutions. Furthermore, the methods of the present invention can be used to improve the detection of cellular spatial organization and the quantification of cellular and tissue natural constituents, domains and structures, including, but not limited to, proteins, genes, DNA sections, subcellular organelles, and the like, using light transmission, reflection, scattering and fluorescence emission strategies, with high spatial and spectral resolutions, and may therefore be employed for classification of cancer cells and/or grading and/or staging the progression of cancer, using, what is referred herein as, spectrally resolved morphometry, mainly for diagnostic and prognostic applications. In particular the methods of the present invention can be used for classification of cells to developmental stages, and to qualify and quantify metabolic processes within cells. The methods can further be used to develop new and more fine tuned indexes for neoplasm classification (including grading), which will eventually replace the existing indexes. Although the explanations and the treatment is shown for full spectral measurements encompassing a large number of wavelengths, it will be recognized on the basis of the description of the method, the assumptions and the provided mathematical modeling, that the method of the present invention is useful and valid for spectral imaging measurements which contain an arbitrary number of wavelengths in the defined spectral range, from one single wavelength to hundreds (the usual maximum number used in this technology), and more.

A spectrometer is an apparatus designed to accept light, to separate (disperse) it into its component wavelengths, and measure the lights spectrum, that is the intensity of the light as a function of its wavelength. An imaging spectrometer is a spectrometer which collects incident light from a scene and measures the spectra of each pixel (i.e., picture element) thereof.

Spectroscopy is a well known analytical tool which has been used for decades in science and industry to characterize materials and processes based on the spectral signatures of chemical constituents therein. The physical basis of spectroscopy is the interaction of light with matter. Traditionally, spectroscopy is the measurement of the light intensity emitted, scattered or reflected from or transmitted through a sample, as a function of wavelength, at high spectral resolution, but without any spatial information.

Spectral imaging, on the other hand, is a combination of high resolution spectroscopy and high resolution imaging (i.e., spatial information). Most of the works so far described concern either obtaining high spatial resolution information from a biological sample, yet providing only limited spectral information, for example, when high spatial resolution imaging is performed with one or several discrete band-pass filters [See, Andersson-Engels et al. (1990) Proceedings of SPIE—Bioimaging and Two-Dimensional Spectroscopy, 1205, pp. 179–189], or alternatively, obtaining high spectral resolution (e.g., a full spectrum), yet limited in spatial resolution to a small number of points of the sample or averaged over the whole sample [See for example, U.S. Pat. No. 4,930,516, to Alfano et al.].

Conceptually, a spectral bio-imaging system consists of (i) a measurement system, and (ii) an analysis software. The measurement system includes all of the optics, electronics and the manner in which the sample is illuminated (e.g., light source selection), the mode of measurement (e.g., fluorescence or transmission), as well as the calibration best suited for extracting the desired results from the measurement. The analysis software includes all of the software and mathematical algorithms necessary to analyze and display important results in a meaningful way.

Spectral imaging has been used for decades in the area of remote sensing to provide important insights in the study of Earth and other planets by identifying characteristic spectral absorption features originating therefrom. However, the high cost, size and configuration of remote sensing spectral imaging systems (e.g., Landsat, AVIRIS) has limited their use to air and satellite-born applications [See, Maymon and Neeck (1988) Proceedings of SPIE—Recent Advances in Sensors, Radiometry and Data Processing for Remote Sensing, 924, pp. 10–22; Dozier (1988) Proceedings of SPIE—Recent Advances in Sensors, Radiometry and Data Processing for Remote Sensing, 924, pp. 23–30].

There are three basic types of spectral dispersion methods that might be considered for a spectral bio-imaging system: (i) spectral grating or prism, (ii) spectral filters and (iii) interferometric spectroscopy. As will be described below, the latter is best suited to implement the method of the present invention, yet as will be appreciated by one ordinarily skilled in the art, grating, prism and filters based spectral bio-imaging systems may also be found useful in some applications.

In a grating or prism (i.e., monochromator) based systems, also known as slit-type imaging spectrometers, such as for example the DILOR system: [see, Valisa et al. (September 1995) presentation at the SPIE Conference European Medical Optics Week, BiOS Europe 1995, Barcelona, Spain], only one axis of a CCD (charge coupled device) array detector (the spatial axis) provides real imagery data, while a second (spectral) axis is used for sampling the intensity of the light which is dispersed by the grating or prism as function of wavelength. The system also has a slit in a first focal plane, limiting the field of view at any given time to a line of pixels. Therefore, a full image can only be obtained after scanning the grating (or prism) or the incoming beam in a direction parallel to the spectral axis of the CCD in a method known in the literature as line scanning. The inability to visualize the two-dimensional image before the whole measurement is completed, makes it impossible to choose, prior to making the measurement, a desired region of interest from within the field of view and/or to optimize the system focus, exposure time, etc. Grating and prism based spectral imagers are in use for remote sensing applications, because an airplane (or satellite) flying over the surface of the Earth provides the system with a natural line scanning mechanism.

It should be further noted that slit-type imaging spectrometers have a major disadvantage since most of the pixels of one frame are not measured at any given time, even though the fore-optics of the instrument actually collects incident light from all of them simultaneously. The result is that either a relatively large measurement time is required to obtain the necessary information with a given signal-to-noise ratio, or the signal-to-noise ratio (sensitivity) is substantially reduced for a given measurement time. Furthermore, slit-type spectral imagers require line scanning to collect the necessary information for the whole scene, which may introduce inaccuracies to the results thus obtained.

Filter based spectral dispersion methods can be further categorized into discrete filters and tunable filters. In these types of imaging spectrometers the spectral image is built by filtering the radiation for all the pixels of the scene simultaneously at a different wavelength at a time by inserting in succession narrow band filters in the optical path, or by electronically scanning the bands using acousto-optic tunable filters (AOTF) or liquid-crystal tunable filter (LCTF), see below. Similarly to the slit type imaging spectrometers equipped with a grating or prism as described above, while using filter based spectral dispersion methods, most of the radiation is rejected at any given time. In fact, the measurement of the whole image at a specific wavelength is possible because all the photons outside the instantaneous wavelength being measured are rejected and do not reach the CCD.

Tunable filters, such as AOTFs and LCTFs have no moving parts and can be tuned to any particular wavelength in the spectral range of the device in which they are implemented. One advantage of using tunable filters as a dispersion method for spectral imaging is their random wavelength access; i.e., the ability to measure the intensity of an image at a number of wavelengths, in any desired sequence without the use of filter wheels. However, AOTFs and LCTFs have the disadvantages of (i) limited spectral range (typically, $\lambda_{max}=2\lambda_{min}$) while all other radiation that falls outside of this spectral range must be blocked, (ii) temperature sensitivity, (iii) poor transmission, (iv) polarization sensitivity, and (v) in the case of AOTFs an effect of shifting the image during wavelength scanning, demanding careful and complicated registration procedures thereafter.

All these types of filter and tunable filter based systems have not been used successfully and extensively over the years in spectral imaging for any application, because of their limitations in spectral resolution, low sensitivity, and lack of easy-to-use and sophisticated software algorithms for interpretation and display of the data.

A method and apparatus for spectral analysis of images which have advantages in the above respects was disclosed in U.S. patent application Ser. No. 08/392,019 to Cabib et al., filed Feb. 21st, 1995, now U.S. Pat. No. 5,539,517, issued Jul. 23, 1996, which is incorporated by reference as if fully set forth herein, with the objective to provide a method and apparatus for spectral analysis of images which better utilizes all the information available from the collected incident light of the image to substantially decrease the required frame time and/or to substantially increase the signal-to-noise ratio, as compared to the conventional slit- or filter type imaging spectrometer, and does not involve line scanning. According to this invention, there is provided a method of analyzing an optical image of a scene to determine the spectral intensity of each pixel thereof by collecting incident light from the scene; passing the light through an interferometer which outputs modulated light corresponding to a predetermined set of linear combinations of the spectral intensity of the light emitted from each pixel; focusing the light outputted from the interferometer on a detector array, scanning the optical path difference (OPD) generated in the interferometer for all pixels independently and simultaneously and processing the outputs of the detector array (the interferograms of all pixels separately) to determine the spectral intensity of each pixel thereof. This method may be practiced by is utilizing various types of interferometers wherein the OPD is varied to build the interferograms by moving the entire interferometer, an element within the interferometer, or the angle of incidence of the incoming radiation. In all of these cases, when the scanner completes one scan of the interferometer, the interferograms for all pixels of the scene are completed.

Apparatuses in accordance with the above features differ from the conventional slit- and filter type imaging spectrometers by utilizing an interferometer as described above, therefore not limiting the collected energy with an aperture or slit or limiting the incoming wavelength with narrow band interference or tunable filters, thereby substantially increasing the total throughput of the system. Thus, interferometer based apparatuses better utilize all the information available from the incident light of the scene to be analyzed, thereby substantially decreasing the measurement time and/or substantially increasing the signal-to-noise ratio (i.e., sensitivity). The sensitivity advantage that interferometric spectroscopy has over the filter and grating or prism methods is known in the art as the multiplex or Fellgett advantage [see, Chamberlain (1979) The principles of interferometric spectroscopy, John Wiley and Sons, pp. 16–18 and p. 263].

Consider, for example, the "whisk broom" design described in John B. Wellman (1987) Imaging Spectrometers for Terrestrial and Planetary Remote Sensing, SPIE Proceedings, Vol. 750, p. 140. Let n be the number of detectors in the linear array, m×m the number of pixels in a frame and T the frame time. The total time spent on each pixel in one frame summed over all the detectors of the array is $nT/m^2$. By using the same size array and the same frame rate in a method according to the invention described in U.S. Pat. No. 5,539,517, the total time spent summed over all the detectors on a particular pixel is the same, $nT/m^2$. However, whereas in the conventional grating or prism method the energy seen by every detector at any time is of the order of 1/n of the total, because the wavelength resolution is 1/n of the range, in a method according to the invention described in U.S. patent application Ser. No. 08/392,019 the energy is of the order of unity, because the modulating function is an oscillating function (e.g., sinusoidal (Michelson) or similar periodic function such as low finesse Airy function with Fabry-Perot) whose average over a large OPD range is 50%. Based on the standard treatment of the Fellgett advantage (or multiplex advantage) described in interferometry textbooks [for example, see, Chamberlain (1979) The principles of interferometric spectroscopy, John Wiley and Sons, pp. 16–18 and p. 263], it is possible to show that devices according to this invention have measurement signal-to-noise ratios which are improved by a factor of $n^{0.5}$ in the cases of noise limitations in which the noise level is independent of signal (system or background noise limited situations) and by the square root of the ratio of the signal at a particular wavelength to the average signal in the spectral range, at wavelengths of a narrow peak in the cases the limitation is due to signal photon noise. Thus, according to the invention described in U.S. Pat. No. 5,539,517, all the required OPDs are scanned simultaneously for all the pixels of the scene in order to obtain all the information required to reconstruct the spectrum, so that the spectral information is collected simultaneously with the imaging information. This invention can be used with many different optical configurations, such as a telescope for remote sensing, a microscope for laboratory analysis, fundus cameras for retinal imaging, fiber optics and endoscopes for industrial monitoring and medical imaging, diagnosis, therapy and others.

In a continuation application (U.S. patent application Ser. No. 08/571,047 to Cabib et al., filed Dec. 12, 1995, now U.S. Pat. No. 5,784,162, issued Jul. 21, 1998, which is incorporated by reference as if fully set forth herein) the objective was to provide spectral imaging methods for biological research, medical diagnostics and therapy, which methods can be used to detect spatial organization (i.e., distribution) and to quantify cellular and tissue natural constituents, structures, organelles and administered components such as tagging probes (e.g., fluorescent probes) and drugs using light transmission, reflection, scattering and fluorescence emission strategies, with high spatial and spectral resolutions. In U.S. Pat. No. 5,784,162 the use of the spectral imaging apparatus described in U.S. Pat. No. 5,539,517 for interphase fluorescent in situ hybridization of as much as six loci specific probes (each loci located on a different chromosome) was demonstrated, as well as additional biological and medical applications.

Spectral bio-imaging systems are potentially useful in all applications in which subtle spectral differences exist between chemical constituents whose spatial distribution and organization within an image are of interest. The measurement can be carried out using virtually any optical system attached to the system described in U.S. Pat. No. 5,539,517, for example, an upright or inverted microscope, a fluorescence microscope, a macro lens, an endoscope and a fundus camera. Furthermore, any standard experimental method can be used, including light transmission (bright field and dark field), auto-fluorescence and fluorescence of administered probes, etc.

Fluorescence measurements can be made with any standard filter cube (consisting of a barrier filter, excitation filter and a dichroic mirror), or any customized filter cube for special applications, provided that the emission spectra fall within the spectral range of the system sensitivity. Spectral bio-imaging can also be used in conjunction with any standard spatial filtering method such as dark field and phase contrast, and even with polarized light microscopy. The effects on spectral information when using such methods must, of course, be understood to correctly interpret the measured spectral images.

U.S. patent application Ser. No. 08/824,234, filed Mar. 25, 1997, which is incorporated by reference as if fully set forth herein teaches methods for automatic and/or semiautomatic spectrally resolved morphometric classification (e.g., detection, grading) of neoplasm, which are designed to provide objective, as opposed to subjective cell (e.g., cancer cell) classification. According to the method disclosed therein (a) a sample including at least a portion of at least one cell is prepared to be spectrally imaged; (b) the sample is viewed through an optical device optically connected to an imaging spectrometer for obtaining a spectrum of each pixel of the sample; (c) each of the pixels is classified into classification groups according to the pixels spectra; and (d) by analyzing the classification groups of pixels, the cells of the sample are classified into cell classes. This method was exemplified with respect to breast carcinomas.

Morphometric classification of various tumor types, such as, but not limited to, leukemias, lymphomas, sarcomas and other carcinomas [see, for example, Clarke A M, Reid W A and Jack A S (1993) Combined proliferating cell nuclear antigen and morphometric analysis in the diagnosis of cancerous lymphoid infiltrates. J. Clin. Pathol. 46:129–134] are vastly implemented both in research medical practice.

Nevertheless, as was recently published following an NIH workshop which evaluated the reliability of histopathological diagnosis by the best pathologists in the field of cancer diagnostics, there is a discordance among expert pathologists in the diagnosis of neoplasm. Based on this workshop, it was concluded that histopathological decision making is 100% subjective, regardless of the origin of specimen and that this state of affairs in histopathological diagnosis is not confined to a specific tumor, but is applicable to differential diagnosis in every organ. These conclusions were published in an editorial by A Bernard Ackerman (1996) entitled "Discordance among expert pathologists in diagnosis of melanocytic neoplasm", in Human pathology 27:1115–1116.

Characterization of nuclear features by different techniques is used for determination of diagnosis, treatment and prognosis. Quantitative estimation of various histopathological parameters such as two dimensional estimates of nuclear profile area, nuclear profile densities and mitotic profile numbers have been shown to correlate with differentiation and prognosis. Alterations in nuclear structure are the morphologic hallmark of cancer diagnosis. Nuclear size, shape, chromatin pattern have all been reported to change in various cancer types. For example, blood cancer cells (e.g., leukemia and lymphoma cells) are unique in their morphological features, which render them amenable for detection and classification via morphometric analysis. The following provides few examples. B-ALL is characterized by lymphoblasts having a small cytoplasm, lacking a nucleolus and having an open chromatin structure. CLL is characterized by small yet apparently mature lymphocytes having a small cytoplasm and condensed chromatin structure. PLL is characterized by lymphocytes having a large cytoplasm, round nucleus and pronounced nucleolus. HCL is characterized by lymphocytes featuring cytoplasmatic projections, giving them a "hairy" appearance. T-ALL is characterized by lymphoblasts having a cleaved or convoluted nucleus and open chromatin structure. Sezary syndrome is characterized by small or large cells featuring cerebriformed nucleus and/or vacuoles and condensed chromatin structure. Additional examples and descriptions associated with these and other diseases and available in Foon K A, Todd R F. Immunologic classification of leukemia and lymphoma. Blood 68:1, 1986; The Non-Hodgkin's lymphoma pathologic classification project: NCI sponsored study of classification of NHL's Summary and description of working formulation for clinical uses. Cancer 49:2112, 1982; A revised European American classification of lymphoid neoplasms: A proposal from the International Lymphoma Study Group. Harris N J et al. Blood 84:1361, 1994, which are incorporated by reference as if fully set forth herein.

All these methods, however, employ only image (i.e., spatial) information for analysis. A whole new dimension of analysis may be added using spectral information which reflects the interaction between light and matter. The combination of both spatial and spectral information will largely contribute to cancer detection and classification.

There is thus a widely recognized need for, and it would be highly advantageous to have, spectral bio-imaging methods and spectral morphometric methods for cells classification devoid of the above described limitations, especially the subjectivity of pathologists in neoplasm diagnosis, which provide advanced and quantitative, semi or fully automatic, means for cancer classification. In addition there a widely recognized need for, and it would be highly advantageous to have, spectral bio-imaging method which accounts for day-to-day variation associated with most of the presently employed cell staining protocols.

SUMMARY OF THE INVENTION

According to the present invention there are provided spectral bio-imaging methods which can be used for automatic and/or semiautomatic spectrally resolved morphometric classification (e.g., grading) of cells (e.g., neoplasm).

The methods can also be used for classification of cells into grades, developmental stages, and to qualify and quantify metabolic processes within cells. The method can further be used to develop new and more fine tuned indexes for neoplasm and embryonic cells classification.

According to further features in preferred embodiments of the invention described below, there is provided a method of spectral-morphometric analysis of biological samples, the biological samples including substantially constant components and suspected variable components, the method comprising the steps of (a) using a spectral data collection device for collecting spectral data of picture elements of the biological samples; (b) defining a spectral vector associated with picture elements representing a constant component of at least one of the biological samples; (c) using the spectral vector for defining a correcting function being selected such that when operated on spectral vectors associated with picture elements representing other constant components, spectral vectors of the other constant components are modified to substantially resemble the spectral vector; (d) operating the correcting function on spectral vectors associated with at least the variable components for obtaining corrected spectral vectors thereof; and (e) classifying the corrected spectral vectors into classification groups.

According to still further features in the described preferred embodiments the method further comprising the step of (f) presenting pixels associated with each of the classification groups in a distinctive color.

According to still further features in the described preferred embodiments the substantially constant components are red blood cells.

According to still further features in the described preferred embodiments the red blood cells are added to the biological sample.

According to still further features in the described preferred embodiments the red blood cells are inherent to the biological sample.

According to still further features in the described preferred embodiments the suspected variable components are tumor cells, tumor tissues or parts thereof.

According to still further features in the described preferred embodiments the tumor cells are hematopoietic tumor cells.

According to still further features in the described preferred embodiments the suspected variable components are cells infected by a pathogen According to still further features in the described preferred embodiments the biological sample is a blood sample of a patient suspected to have or having a hematopoietic tumor.

According to still further features in the described preferred embodiments the hematopoietic tumor is selected from the group consisting of leukemia and lymphoma.

According to still further features in the described preferred embodiments the biological sample is of a patient suspected of having or having a disease selected from the group consisting of ALL, CLL, IM, PCL, PLL and Sezary syndrome.

According to still further features in the described preferred embodiments prior to collecting spectral data of picture elements of the biological samples, the biological sample is stained.

According to still further features in the described preferred embodiments staining the biological sample is effected via a stain selected from the group consisting of an immunohistochemical stain, a histological stain, a DNA ploidy stain, a nucleic acid sequence specific probe and any combination thereof.

According to still further features in the described preferred embodiments the histological stain is selected from the group consisting of Hematoxylin-Eosin stain, May Grunwald Giemsa stain, Romanowsky Giemsa, Masson's trichrome and Papanicolaou stain.

According to still further features in the described preferred embodiments collecting spectral data of picture elements of the biological samples is effected by (i) collecting incident light simultaneously from all pixels of the sample using collimating optics; (ii) passing the incident collimated light through an interferometer system having a number of elements, so that the light is first split into two coherent beams which travel in different directions inside the interferometer and then the two coherent beams recombine to interfere with each other to form an exiting light beam; (iii) passing the exiting light beam through a focusing optical system which focuses the exiting light beam on a detector having a two-dimensional array of detector elements, so that at each instant each of the detector elements is the image of one and always the same pixel of the sample for the entire duration of the measurement, so that the real image of the sample is stationary on the plane of the detector array and at any time during the measurement the image is still visible and recognizable, and so that each of the detector elements produces a signal which is a particular linear combination of light intensity emitted by the pixel at different wavelengths, wherein the linear combination is a function of the instantaneous optical path difference; (iv) scanning one or more of the elements of the interferometer system, so that the optical path difference between the two coherent beams generated by the interferometer system is scanned simultaneously for all the pixels of the sample; and (v) recording signals of each of the detector elements as function of time using a recording device to form a spectral cube of data.

According to still further features in the described preferred embodiments collecting spectral data of picture elements of the biological samples is effected by (i) illuminating the sample with broadband light through a step-scan interferometer and condenser; (ii) collecting and optically imaging transmitted or reflected light through the sample onto a two-dimensional array of detector elements (such as a CCD or focal plane array); (iii) recording a number of frames from all the pixels of the sample in synchronization with each step-scanned position of the interferometer; (iv) mathematically processing each interferogram function so obtained for each pixel of the image to obtain a spectrum as function of wavelength for each of said pixels; and optionally, (v) performing spectral correction, classification or color display of the pixels based on their so obtained and corrected spectral vectors, as described herein.

According to still further features in the described preferred embodiments the spectral data collection device includes an element selected from the group consisting of a dispersion element, a filter and an interferometer.

According to still further features in the described preferred embodiments classifying the corrected spectral vectors into classification groups is effected using a classification map algorithm which employs reference spectral vectors for associating picture elements into the classification groups.

According to still further features in the described preferred embodiments the reference spectral vectors for classification are of a previously prepared reference library.

According to still further features in the described preferred embodiments at least one of the reference spectral vectors for classification is of picture elements derived from a cell domain selected from the group consisting of nucleolus, inter-chromosomal region, cytoplasm, a first chromatin region of the nucleus, a second chromatin region of the nucleus and background.

According to still further features in the described preferred embodiments the spectral vector is a normalized spectral vector.

According to still further features in the described preferred embodiments classifying the corrected spectral vectors into classification groups is effected by spectral vector maxima classification.

The present invention successfully addresses the shortcomings of the presently known configurations by providing a method for automatic or semi automatic and internally referenced method for classification and grading of neoplasm. Furthermore, the method of the present invention provides spectrally resolved morphometric classification images which may be used by pathologists for classification and grading of neoplasm, which images replace the prior art RGB images and lead to more objective interpretation of the results and therefore, to a more accurate classification. This in turn may affect diagnosis, treatment and prognosis.

BRIEF DESCRIPTION OF THE DRAWINGS

The file of this patent contains at least one drawings executed in color photograph. Copies of this patent with color photograph(s) will be provided by the Patent and Trademark Office upon request and payment of necessary fee.

The invention herein described, by way of example only, with reference to the accompanying drawings, wherein.

DESCRIPTION OF THE PREFERRED EMBODIMENTS

The present invention is of standardization of spectral measurements which can be used to allow automatic and/or semiautomatic spectrally resolved morphometric classification (e.g., grading) of cells (e.g., neoplasm, embryonic cells, etc.), despite the well known difficulties encountered in this field due to staining variability and/or instrumental drifts. Specifically, the present invention can be used to detect cellular spatial organization and to quantify cellular and tissue constituents and structures associated with tumorogenesis using light transmission microscopy combined with high spatial and spectral resolutions. This includes staining of cytological preparations or tissue sections with chromogenic dyes in the presence or absence of additional stained and/or tagged probes for the detection of protein and/or nucleic acid markers. The methods can also be used for classification of cells into developmental stages, and to qualify and quantify metabolic processes within cells. The method can further be used to develop new and more fine tuned indexes for neoplasm classification, bacterial infections, and other pathological states.

Spectral Imaging Systems

For purposes of better understanding the present invention, as illustrated in FIGS. 4–14 of the drawings, reference is first made to the construction and operation of some spectral imaging systems (i.e., imaging spectrometers).

Figure 1:
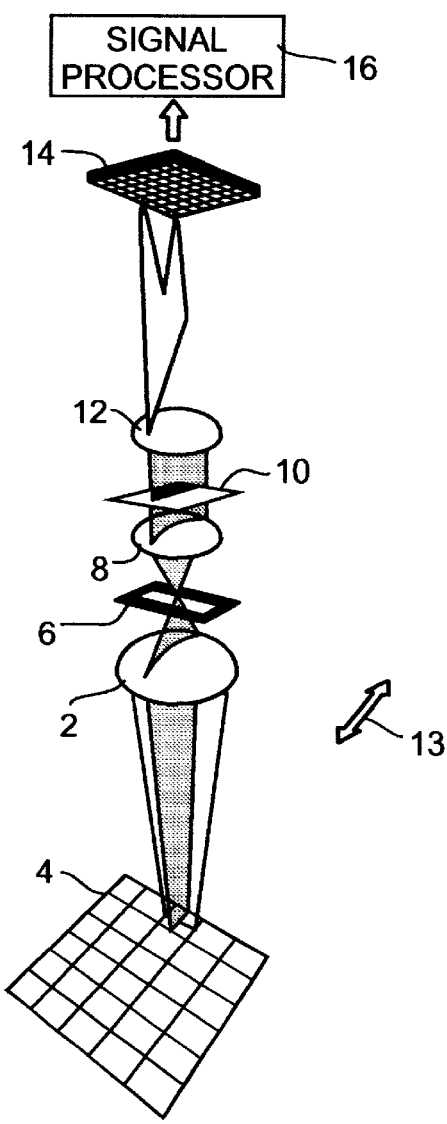
FIG. 1 illustrates a conventional (prior art) slit-type imaging spectrometer.

A conventional (i.e., prior art) slit-type imaging spectrometer utilizing a two-dimensional array of detectors as illustrated in FIG. 1.

Thus, the prior art slit-type imaging spectrometer as illustrated in FIG. 1 comprises a collection optical system as indicated at 2, for collecting the incident is light from a scene, schematically indicated at 4 and focusing the substantially parallel light of the scene 4 onto a first focal plane occupied by a slit 6 to define the field of view. The light exiting from slit 6 is collimated in a collimator lens 8 and is passed through a spectral dispersion element 10 (e.g., a grating or a prism) to separate the various wavelengths. The output from spectral dispersion element 10 is focused by a focusing lens 12 onto a two-dimensional detector array 14 in a second focal plane. The output of detector array 14 is fed to a signal processor 16.

In the two-dimensional array of detectors 14 illustrated in the prior art imaging spectrometer of FIG. 1, the movement of the system (e.g., a raster movement or line scanning indicated by arrow 13) effects the scanning along one dimension. The scanning along the second dimension is effected by the slit 6 which is oriented perpendicularly to the direction of movement of the system. The slit 6 thus assures that each detector within the array 14 sees only the contribution of one pixel at a single wavelength at any time. This is necessary to separate the spectra of each pixel.

As mentioned in the background section and hereinabove, the disadvantage of the prior art method illustrated in FIG. 1 is that most of the pixels of one frame are not measured at any given time even though the optical system 2 actually collects light energy from all of them simultaneously. As a result, the required frame time is significantly increased, and/or the signal-to-noise ratio (sensitivity) is substantially decreased with respect to a system which does not have the need for such a slit.

Figure 2:
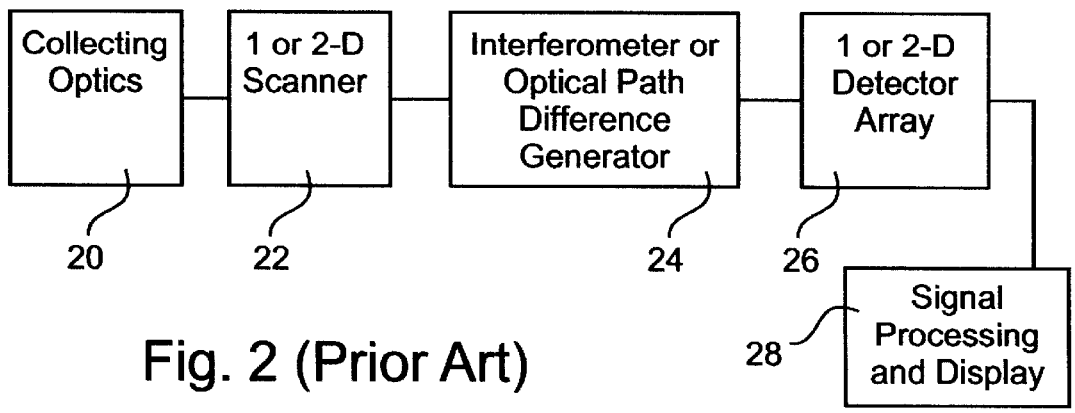
FIG. 2 is a block diagram illustrating the main components of an imaging spectrometer constructed in accordance with U.S. Pat. No. 5,539,517 (prior art).

FIG. 2 is a block diagram illustrating the main components of an improved prior art imaging spectrometer disclosed in U.S. patent application Ser. No. 08/392,019 to Cabib et al., filed Feb. 21st, 1995, now U.S. Pat. No. 5,539,517, issued Jul. 23, 1996, which is incorporated by reference as if fully set forth herein. This imaging spectrometer is constructed highly suitable to implement the methods of the present invention.

Thus, the prior art imaging spectrometer of FIG. 2 includes: a collection optical system, generally designated 20; a one-dimensional scanner, as indicated by block 22; an optical path difference (OPD) generator or interferometer, as indicated by block 24; a one-dimensional or two-dimensional detector array, as indicated by block 26; and a signal processor and display, as indicated by block 28.

A critical element in system 20 is the OPD generator or interferometer 24, which outputs modulated light corresponding to a predetermined set of linear combinations of the spectral intensity of the light emitted from each pixel of the scene to be analyzed. The output of the interferometer is focused onto the detector array 26. Thus, all the required optical phase differences are scanned simultaneously for all the pixels of the field of view, in order to obtain all the information required to reconstruct the spectrum of each pixel. The spectra of all the pixels in the scene are thus collected simultaneously with the imaging information, thereby permitting analysis of the image in a real-time manner.

The apparatus according to U.S. Pat. No. 5,539,517 may be practiced in a large variety of configurations. Specifically, the interferometer used may be combined with other mirrors as described in the relevant Figures of U.S. Pat. No. 5,539,517.

Thus, according to U.S. Pat. No. 5,539,517, few alternative types of interferometers may be employed. These include (i) a moving type interferometer in which the OPD is varied to modulate the light, namely, a Fabry-Perot interferometer with scanned thickness; (ii) a Michelson type interferometer which includes a beamsplitter receiving the beam from an optical collection system and a scanner, and splitting the beam into two paths; (iii) a Sagnac interferometer optionally combined with other optical means in which interferometer the OPD varies with the angle of incidence of the incoming radiation, and (iv) a four-mirror plus beamsplitter interferometer as further described and exemplified in the cited U.S. Pat. application.

Figure 3:
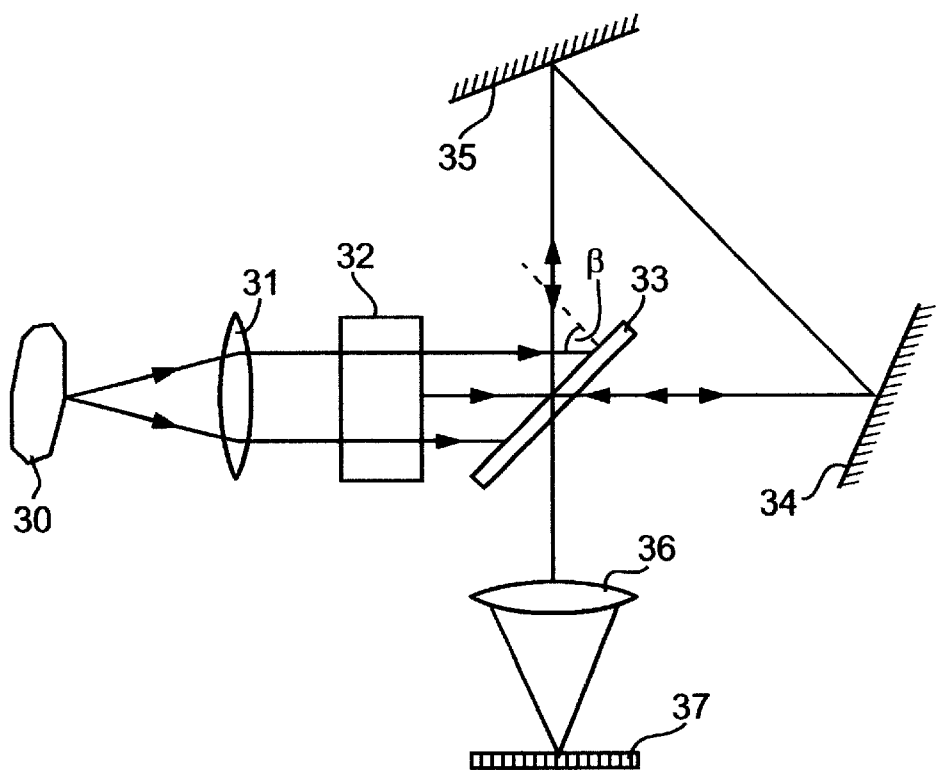
FIG. 3 illustrates a non-moving type interferometer, namely, a Sagnac interferometer, as used in an imaging spectrometer in accordance with U.S. Pat. No. 5,539,517 (prior art).

FIG. 3 illustrates an imaging spectrometer constructed in accordance with U.S. Pat. No. 5,539,517 utilizing an interferometer in which the OPD varies with the angle of incidence of the incoming radiation. A beam entering the interferometer at a small angle to the optical axis undergoes an OPD which varies linearly with this angle.

In the interferometer of FIG. 3, all the radiation from source 30 in all the pixels, after being collimated by an optical collection system 31, is scanned by a mechanical scanner 32. The light is then passed through a beamsplitter 33 to a first reflector 34 and then to a second reflector 35, which reflects the light back through the beamsplitter 33 and then through a focusing lens 36 to an array of detectors 37 (e.g., a CCD). This beam interferes with the beam which is reflected by 33, then by second reflector 35, and finally by first reflector 34.

An imaging spectrometer in accordance with the invention disclosed in U.S. Pat. No. 5,539,517 was developed by Applied Spectral Imaging (ASI) Ltd., Industrial Park, Migdal Haemek, Israel and is referred hereinbelow as SPECTRACUBE™. The SPECTRACUBE™ system optically connected to a variety of optical devices was used to implement the methods of the present invention. The SPECTRACUBE™ system has the following characteristics, listed hereinbelow in Table 1:

TABLE 1

| Parameter | Performance |
|---|---|
| Spatial resolution: | 30/M μm (M = effective microscope or fore optics magnification) |
| Field of View: | 8/M millimeter |
| Sensitivity: | 20 milliLux (for 100 msec integration time, increases for longer integration times linearly with √T) |
| Spectral range: | 400–1000 nm |
| Spectral resolution: | 4 nm at 400 nm (16 nm at 800 nm) |
| Acquisition time: | 5–50 sec, typical 15–25 sec |
| FFT processing time: | 20–180 sec, typical 60 sec |

The SPECTRACUBE™ system easily attaches to any microscope or macro lens with, for example, C-mount or F-mount connectors, and can stand in any orientation during the measurement. The system may as well be connected to other magnification means and to various types of endoscopes and cameras. Therefore, spectral images of cells and tissues in various magnification and lighting strategies may be obtained.

The SPECTRACUBE™ system has numerous utilities. For examples of the use of the SpectaCube™ system for various biological applications, the reader is referred to U.S. patent application Ser. No. 08/571,047, and to E. Schroeck et al. (1996) Multicolor spectral karyotyping of human chromosomes. Science, 273, 494–497; Garini et al. (1996) Spectral Karyotyping, Bioimaging 4, 65–72; Malik et al. (1996) Fourier transform multipixel spectroscopy and spectral imaging of protoporphyrin in single melanoma cells, Photochemistry and photobiology 63, 608–614; Malik et al. (1996) Fourier transform multipixel spectroscopy for quantitative cytology, Journal of Microscopy 182, 133–140; Garini et al. (1996) Spectral Bio-Imaging, Fluorescence imaging spectroscopy and microscopy, chapter 4, ed. X. F. Wang and B. Herman, Chemical Analysis Series, Vol. 137, John Wiley and Sons; Soenksen et al. (1996) Use of novel spectral bio-imaging system as an imaging oximeter in intact rat brain, SPIE Proceedings 2679; Liyanage et al. (1996) Multicolor spectral karyotyping of mouse chromosomes, Nature Genetics 14, 312–315; all are incorporated by reference as if fully set forth herein.

The prior art SPECTRACUBE™ system is used herein to acquire spectral data of every pixel of cancer cells. However, any spectral imager, i.e., an instrument that measures and stores in memory for later retrieval and analysis the spectrum of light emitted by every point of an object which is placed in its field of view, including filter (e.g., acousto-optic tunable filters (AOTF) or liquid-crystal tunable filter (LCTF)) and dispersive element (e.g., grating or prism) and spectral imagers based on interferometers built in a different configuration than SPECTRACUBE, can be used to acquire the required spectral data. Therefore, it is intended not to limit the scope of the present invention for use of any specific type of spectral imager.

Display and Analysis of Spectral Images a. General

As mentioned above, a spectral image is a three dimensional array of data, I(x,y,λ), that combines spectral information with spatial organization of the image. As such, a spectral image is a set of data called a spectral cube, due to its dimensionality, which enables the extraction of features and the evaluation of quantities that are difficult, and in some cases even impossible, to obtain otherwise. Since both spectroscopy and digital image analysis are well known fields that are covered by an enormous amount of literature [see, for example, Jain (1989) Fundamentals of Digital Image Processing, Prentice-Hall International], the following discussion will focus primarily on the benefit of combining spectroscopic and imaging information in a single data set, i.e., a spectral cube.

One possible type of analysis of a spectral cube is to use spectral and spatial data separately, i.e., to apply spectral algorithms to the spectral data and two-dimensional image processing algorithms to the spatial data.

As an example for a spectral algorithm consider an algorithm computing the similarity between a reference spectrum and the spectra of all pixels (i.e., similarity mapping) resulting in a gray (or other color) scale image (i.e., a similarity map) in which the intensity at each pixel is proportional to the degree of 'similarity'. This gray scale image can then be further analyzed using image processing and computer vision techniques (e.g., image enhancement, pattern recognition, etc.) to extract the desired features and parameters. In other words, similarity mapping involves computing the integral of the absolute value of the difference between the spectrum of each pixel of the spectral image with respect to a reference spectrum (either previously memorized in a library, or belonging to a pixel of the same or other spectral image), and displaying a gray level or pseudocolor (black and white or color) image, in which the bright pixels correspond to a small spectral difference, and dark pixels correspond to a large spectral difference, or vice versa.

Similarly, classification mapping perform the same calculation as described for similarity mapping, yet takes several spectra as reference spectra, and paints each pixel of the displayed image with a different predetermined pseudocolor, according to its classification as being most similar to one of the several reference spectra. Both, similarity and classification mapping may employ any of the four following Equations.

The reference spectrum can be one corresponding to a pixel in the same image, or from a library or from another image.

There are many similarity map functions known in the literature, four are given hereinbelow:

$$G_{x,y}^{(1)} = \frac{I_{max}^2}{40\left(\left(\frac{1}{n}\sum_\lambda (I_{xy}(\lambda) - R_\lambda)^2\right)^{\frac{1}{2}} + \frac{I_{max}}{40}\right)}$$

$$G_{x,y}^{(2)} = \frac{I_{max}^2}{20\left(\left(\frac{1}{n}\sum_\lambda (I_{xy}(\lambda) - R_\lambda)^2\right)^{\frac{1}{2}} + \frac{I_{max}}{20}\right)}$$

$$G_{x,y}^{(3)} = \frac{I_{max}^2}{40\left(\frac{R_{max}}{S_{max}}\left(\frac{1}{n}(I_{xy}(\lambda) - R_\lambda)^2\right)^{\frac{1}{2}} + \frac{I_{max}}{40}\right)}$$

$$G_{x,y}^{(4)} = \frac{I_{max}^2}{40\left(\frac{R_{max}}{T_{max}}\left(\frac{1}{n}(\langle I_{xy}(l)\rangle - R_l)^2\right)^{\frac{1}{2}} + \frac{I_{max}}{40}\right)}$$

where $I_{max}$ is the maximum intensity of the image, $G_{x,y}$ is the brightness with which a pixel (of coordinates x and y) is displayed on the screen, $I_{x,y}(\lambda)$ is its spectrum, $\langle I_{x,y}(\lambda)\rangle$ is the average of $I_{xy}(\lambda)$ over the group of 3×3 neighboring pixels, $S_{max}$ is the peak intensity of $I_{xy}(\lambda)$, $T_{max}$ is the peak intensity of $<I_{xy}(\lambda)>$, $R_\lambda$ is the reference spectrum with respect to which the similarity map is calculated, $R_{max}$ is the peak intensity of the reference spectrum $R_\lambda$ and n is the number of wavelengths of the measurement.

When similarity mapping is performed, it is clear that according to the above Equations, in all cases, the more a pixel spectrum is similar to the reference spectrum, the brighter it will be displayed on the screen.

On the other hand, when classification is performed, a calculation using the spectrum of each of the pixels of the image, one at a time, and of each of the few reference spectra, one at a time, is performed (preferably after normalization of all spectra to a 0–100 % intensity range), and the analyzed pixel is given a preselected arbitrary color according to the reference spectra to which it is most similar using for example a minimal square error calculation, as well known in the art.

It is also possible to apply spectral image algorithms based on non-separable operations; i.e., algorithms that include both local spectral information and spatial correlation between adjacent pixels (one of these algorithms is, as will be seen below, a principal component analysis).

One of the basic needs that arise naturally when dealing with any three-dimensional (3D) data structure such as a spectral cube (i.e., $I(x,y,\lambda)$), is visualizing that data structure in a meaningful way. Unlike other types of 3D data such as topographic data, $D(x,y,z)$, obtained for example by a confocal microscope, where each point represents, in general, the intensity at a different locations (x,y,z) in tree-dimensional space, a spectral image is a sequence of images representing the intensity of the same two-dimensional plane (i.e., the sample) at different wavelengths. For this reason, the two most intuitive ways to view a spectral cube of data is to either view the image plane (spatial data) or the intensity of one pixel or a set of pixels as function of wavelength in a three-dimensional mountain-valley display. In general, the image plane can be used for displaying either the intensity measured at any single wavelength or the gray scale image that results after applying a spectral analysis algorithm, over a desired spectral region, at every image pixel. The spectral axis can, in general, be used to present the resultant spectrum of some spatial operation performed in the vicinity of any desired pixel (e.g., averaging the spectrum).

It is possible, for example, to display the spectral image as a gray scale image, similar to the image that might be obtained from a simple monochrome camera, or as a multicolor image utilizing one or several artificial colors to highlight and map important features. Since such a camera simply integrates the optical signal over the spectral range (e.g., 400 nm to 760 nm) of the CCD array, the 'equivalent' monochrome CCD camera image can be computed from the 3D spectral image data base by integrating along the spectral axis, as follows:

$$\text{gray\_scale}(x, y) = \int_{\lambda_2}^{\lambda_1} w(\lambda) \cdot I(x, y, \lambda) d\lambda$$

In the above Equation, $w(\lambda)$ is a general weighting response function that provides maximum flexibility in computing a variety of gray scale images, all based on the integration of an appropriately weighted spectral image over some spectral range. For example, by evaluating the above Equation with three different weighting functions, $\{W_r(\lambda), w_g(\lambda), W_b(\lambda)\}$, corresponding to the tristimulus response functions for red (R), green (G) and blue (B), respectively, it is possible to display a conventional RGB color image. It is also possible to display meaningful non-conventional (pseudo) color images.

Figure 4:
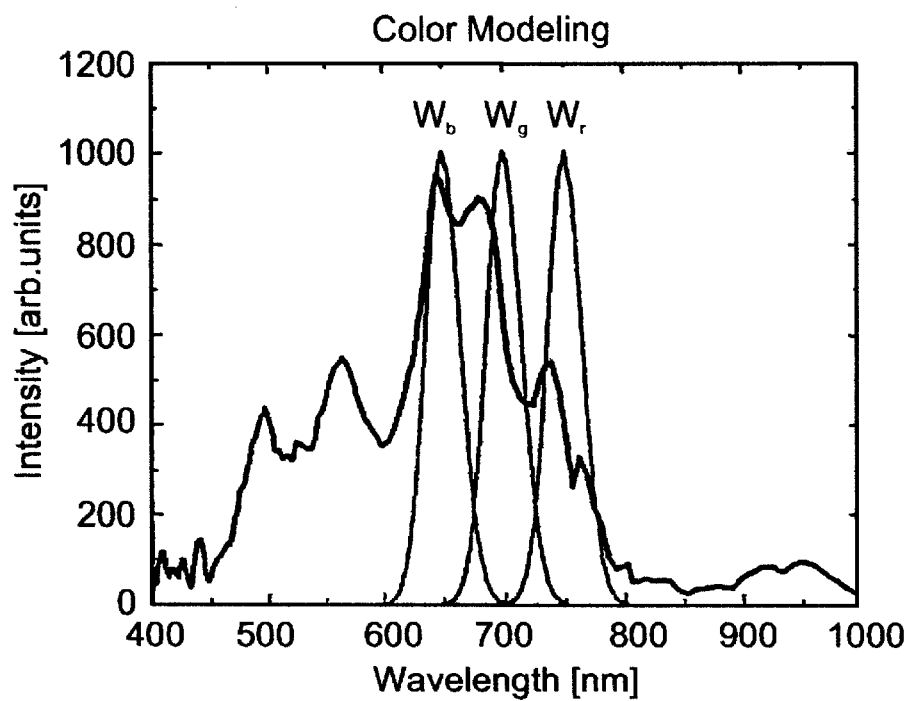
FIG. 4 shows a definition of pseudo-RGB (Red, Green and Blue) colors for emphasizing chosen spectral ranges. The intensity for each of the RGB components is calculated by integrating the area under the spectrum of the pixel, after multiplying it by one of the three curves.

FIG. 4 presents an example of the power of this simple algorithm. Consider choosing $\{W_r, W_g, W_b\}$ to be Gaussian functions distributed "inside" a spectrum of interest, the resulting pseudo-color image that is displayed in this case emphasizes only data in the spectral regions corresponding to the weighting functions, enabling spectral differences in these three regions to be detected more clearly.

b. Point operations

Point operations are defined as those that are performed on single pixels, (i.e., do not involve more than one pixel at a time). For example, in a gray scale image, a point operation can be one that maps the intensity of each pixel (intensity function) into another intensity according to a predetermined transformation function. A particular case of this type of transformation is the multiplication of the intensity of each pixel by a constant.

The concept of point operations can also be extended to spectral images: here each pixel has its own intensity function (spectrum), i.e., an n-dimensional vector $V_1(\lambda)$; $\lambda \in [\lambda_1, \lambda_n]$. A point operation applied to a spectral image can be defined as one that maps the spectrum of each pixel into a scalar (i.e., an intensity value) according to a transformation function:

$$v_2 = g(V_1(\lambda)); \lambda \in [\lambda_1, \lambda_n]$$

Building a gray scale image according to the above Equation is an example of this type of point operation. In the more general case, a point operation maps the spectrum (vector) of each pixel into another vector according to a transformation function:

$$V_2(l) = g(V_1(\lambda)); l \in [1, N], \lambda \in [\lambda_1, \lambda_n],$$

where $N \leq n$.

In this case a spectral image is transformed into another spectral image.

One can now extend the definition of point operations to include operations between corresponding pixels of different spectral images. An important example of this type of algorithm is optical density analysis. Optical density is employed to highlight and graphically represent regions of an object being studied spectroscopically with higher dynamic range than the transmission spectrum. The optical density is related to transmission by a logarithmic operation and is therefore always a positive function. The relation between the optical density and the measured spectra is given by Lambert Beer law:

$$OD(\lambda) = -\log_{10} \frac{I(\lambda)}{I_0(\lambda)} = -\log_{10} \tau(\lambda)$$

where $OD(\lambda)$ is the optical density as a function of wavelength, $I(\lambda)$ is the measured spectrum, $I_0(\lambda)$ is a measured reference spectrum, and $\tau(\lambda)$ is the spectral transmittance of the sample. The above Equation is calculated for every pixel for every wavelength where $I_0(\lambda)$ is selected from (i) a pixel in the same spectral cube for which OD is calculated; (ii) a corresponding pixel in a second cube; and (iii) a spectrum from a library.

Note that the optical density does not depend on either the spectral response of the measuring system or the non-uniformity of the CCD detector. This algorithm is useful to map the relative concentration, and in some cases the absolute concentration of absorbers in a sample, when their absorption coefficients and the sample thickness are known.

Additional examples include various linear combination analyses, such as for example: (i) applying a given spectrum to the spectrum of each of the pixels in a spectral image by an arithmetical function such as addition, subtraction, multiplication division and combinations thereof to yield a new spectral cube, in which the resulting spectrum of each pixel is the sum, difference, product ratio or combination between each spectrum of the first cube and the selected spectrum; and (ii) applying a given scalar to the spectra of each of the pixels of the spectral image by an arithmetical function as described above.

Such linear combinations may be used, for example, for background subtraction in which a spectrum of a pixel located in the background region is subtracted from the spectrum of each of the pixels; and for a calibration procedure in which a spectrum measured prior to sample analysis is used to divide the spectrum of each of the pixels in the spectral image.

Another example includes a ratio image computation and display as a gray level image. This algorithm computes the ratio between the intensities at two different wavelengths for every pixel of the spectral image and paints each of the pixels in a lighter or darker artificial color accordingly. For example, it paints the pixel bright for high ratio, and dark for low ratio (or the opposite), to display distributions of spectrally sensitive materials.

c. Spatial-spectral combined operations

In all of the spectral image analysis methods mentioned above, algorithms are applied to the spectral data. The importance of displaying the spectrally processed data as an image is mostly qualitative, providing the user with a useful image. It is also possible, however, depending on the application, to use the available imaging data in even more meaningful ways by applying algorithms that utilize the spatial-spectral correlation that is inherent in a spectral image. Spatial-spectral operations represent the most powerful types of spectral image analysis algorithms. As an example, consider the following situation:

A sample contains k cell types stained with k different fluorophores (the term 'cell' here is used both for a biological cell, and also as 'a region in the field of view of the instrument'). Each fluorophore has a distinct fluorescence emission spectrum and binds to only one of the k cell types. It is important to find the average fluorescence intensity per cell for each one of the k cell types. To achieve this task the following procedure can be used: (i) classify each pixel in the image as belonging to one of k+1 classes (k cell types plus a background) according to its spectrum; (ii) segment the image into the various cell types and count the number of cells from each type; and (iii) sum the fluorescence energy contributed by each class, and divide it by the total number of cells from the corresponding class.

This procedure makes use of both spectral and spatial data. The relevant spectral data takes the form of characteristic cell spectra (i.e., spectral "signatures"), while the spatial data consists of data about various types of cells (i.e., cell blobs) many of which appear similar to the eye. The ideal type of measurement for this type of situation is a spectral image. In the above situation, cells can be differentiated by their characteristic spectral signature. Hence, a suitable point operation will be performed to generate a synthetic image in which each pixel is assigned one of k+1 values. Assuming that the fluorescence emission spectra of the different cell types are known to be $s_i(\lambda)$; i=1, 2 ..., k, $\lambda \in [\lambda_1, \lambda_n]$, and the measured spectrum at each pixel (x, y) is $s_{x,y}(\lambda)$, $\lambda \in [\lambda_1, \lambda_n]$, then the following algorithm is a possible method of classification (step 1 above):

Let $e^2_i$ be the deviation of the measured spectrum from the known spectrum of the fluorophore attached to cell type i. Then, adopting a least-squares "distance" definition, one can write:

$$e_i^2 = \sum_{\lambda \in R_\lambda} (s(\lambda) - s_i(\lambda))^2$$

where $R_\lambda$ is the spectral region of interest. Each point [pixel (x, y)] in the image can then be classified into one of the k+1 classes using the following criterion:

point(x,y)∈ class k+1 if $e^2_i$>threshold for all i∈[l,k], whereas point(x,y)∈ class ρ if $e^2_i$<threshold, and ρ is such that min[$e^2_i$]=$e^2_\rho$ Image segmentation and calculation of average fluorescence intensity are now straightforward using standard computer vision operations on the synthetic image created in accordance with the algorithm described in last two equations.

Another approach is to express the measured spectrum $s_{x,y}(\lambda)$ at each pixel as a linear combination of the k known fluorescence spectra $s_i(\lambda)$; i=1, 2, . . . , k. In this case one would find the coefficient vector C=[$c_1$, $c_2$, . . . , $c_k$] that solves:

$$F = \min \sum_{\lambda \in R_\lambda} (s(\lambda) - \hat{s}(\lambda))^2$$

where $$\hat{s}(\lambda) = \sum_{i=1}^{k} c_i \cdot s_i(\lambda),$$

Solving for $$\frac{dF}{dc_i} = 0;$$

for i=1, 2, . . . , k (i.e., find values of $c_i$ which minimize F) yields the matrix Equation C=$A^{-1}$ B, where A is a square matrix of dimension k with elements $$a_{m,n} = \left[\sum_{\lambda \in R_\lambda} s_m(\lambda) \cdot s_n(\lambda)\right],$$

and B is a vector defined as $$b_m = \left[\sum_{\lambda \in R_\lambda} s_m(\lambda) \cdot s(\lambda)\right],$$

m, n=1, 2, . . . , k.

Arithmetic operations may similarly be applied to two or more spectral cubes and/or spectra of given pixels or from a library. For example consider applying an arithmetic operations between corresponding wavelengths of corresponding pairs of pixels belonging to a first spectral cube of data and a second spectral cube of data to obtain a resulting third spectral cube of data for the purpose of, for example, averaging two spectral cubes of data, time changes follow-up, spectral normalization, etc.

In many cases, objects (e.g., cancer cells) present in a spectral image differ from one another in chemical constituents and/or structure to some degree. Using a decorrelation statistical analysis such as principal component analysis by producing covariance or correlation matrices enhances these small differences.

Decorrelation statistical analysis is directed at extracting decorrelated data out of a greater amount of data, and average over the correlated portions thereof. There are a number of related statistical decorrelation methods. Examples include but not limited to principal component analysis (PCA), canonical variable analysis and singular value decomposition, etc., of these methods PCA is perhaps the more common one, and is used according to the present invention for decorrelation of spectral data. However, considering the fact that all decorrelation statistical methods including those listed above are related to one another, there is no intention to limit the scope of the invention to use of any specific decorrelation method. Specifically, there is no intention to limit the scope of the present invention to use of principal component analysis, as any other decorrelation statistical method may be alternatively employed. Information concerning the use and operation of the above listed decorrelation statistical methods is found in R. A. Johnson and D. W. Wichen, "Applied Multivariance Statistical Analysis, third edition, Prentice Hall (1992) and T. W. Anderson, An Introduction to Multivariance Statistical Analysis, second edition, Wiley and Sons (1984), both are incorporated by reference as if fully set forth herein.

Furthermore, as will become apparent from the descriptions to follow, the implementation of a decorrelation statistical method may be done using various modifications. As the concept of the present invention is not dependent upon any specific modification, it is the intention that the scope of the present invention will not be limited to any specific modification as described below.

Principal component analysis (PCA) is one of a number of powerful techniques used in multivariate statistical analysis. It is advantageous in cases where a large number of "results", which depend on a large number of possibly correlated variables forms the basic data set. Its strength lies in the fact that this data decomposition provides a transformation to decorrelated variables, while simultaneously averaging over correlated variables.

In this paragraph the PCA technique as applied to multi-spectral images of the same object is delineated. The basic data set, i.e., the spectral cube, is composed of k spectral slices of the same object, where each spectral slice is obtained at a different spectral band. Thus, the data set is composed of the spectra of all the pixels of the object. One of the objectives of looking at such a data set can be the characterization of the pixels into groups of similar spectra. Regard each spectral slice as a vector whose elements are the image pixels arranged into the column vector using a predetermined code. Call the spectral slices $X_m$, so that the term $x_{nm}$ signifies the n-th pixel of the m-th spectral slice. In such way, the matrix $x=\{x_{nm}\}$ carries the full information, so that each column is a spectral slice. Define a matrix y derived from matrix x by subtracting from each column, the column average. The various columns of the y matrix may be correlated, so that, some of the information carried by the data is correlated. The PCA technique decorrelates the information and reduces it only to decorrelated variables, so that the amount of "real" data pixels is smaller and easier to handle.

The correlations are obtained directly by computing the covariance matrix c defined by:

$$c=y'y$$

where y' is the transpose of y. The i,j term of c is the covariance of the i-th slice with the j-th slice, i.e. if they are decorrelated this term vanishes. The diagonal of c is composed of the variances of each spectral slice, which can be regarded as a scale for the amount of information in this particular slice. Alternatively, this variance (its square root) can be regarded as the average contrast of this particular slice.

Linear algebra describes this situation as follows. The objects of interest (the pixels of the spectral slices, k of them) are points in a k dimensional space. The fact that the covariance matrix c shows correlations is represented by its having a rank smaller than k. This situation is called degeneracy and it means that the k (narrow band) spectral slices provide too much data relative to the information content. Reduction of the data is performed by finding the eigen system of the covariance matrix. Formally, this operation means that one has to find k vectors $v_m$ called eigenvectors and k scalars $\lambda_m$ called eigenvalues so that:

$$c.v_m = \lambda_m v_m \text{ for } m=1, 2, \ldots, k$$

In a case where the data is correlated, some of the eigenvalues vanish. The number of non-vanishing eigenvalues defines the dimension of the information, which dimension is smaller than k. The corresponding eigenvectors define a subspace in the original k space in which the full information content is represented. Furthermore, the information in each new dimension is completely decorrelated to the information in the other dimensions. Thus in the new space the full information content is represented in a decorrelated manner so that it can be easily used for classification purposes. For further details regarding the principal component analysis, the reader is referred to Martens and Naes (1989) Multivariate Calibration, John Wiley & Sons, Great Britain; and to Esbensen et al., Eds. (1994) Multi variance analysis—in practice; and, Computer-aided modeling as CAMO, and the Unscrambler's User's guide, Trondheim, Norway, both are incorporated by reference as if fully set forth herein.

It should be noted that such an analysis can be performed on a whole spectral cube. Preferably, the analysis is performed only for selected pixels or mathematically manipulated (e.g., after background subtraction and averaging) selected pixels to improve the results and enable better classification later on. The preferred approach is described in more detail below, nevertheless, there is no intention to limit the scope of the present invention to the preferred approach employed, as different mathematical manipulations may be found useful for different data collection approaches (e.g., filter or dispersion element based spectral imagers).

Transmission Microscopy

Light microscopy is one of the most fundamental techniques for the visualization of cells and tissues in biology and pathology. Transmission microscopy suffers greatly from the inherently low contrast of cell organelles and structural details. Many methods have been developed to improve this contrast, among them staining, spatial filtering and others. The use of the spectral bio-imaging methods of the present invention with stained cells and tissues is one of the most straightforward methods to increase even further their apparent contrast, when examined under a transmission microscope, thereby improving dramatically the identification and discrimination capabilities of this popular microscopic method. The basic approach proposed herein is to measure a spectral image, and to then use this large amount of information in conjunction with spectral and morphological analysis methods and algorithms in order to identify and map cellular and subcellular details.

In order to facilitate the histological examination of biological specimens, a variety of staining techniques were developed during the last century using organic stains which specifically bind to different macromolecules in the cells, though the molecular basis of the staining techniques has been and still is empirical. Other image contrast enhancement methods include the use of spatial filtering techniques such as dark field and polarization methods [see, Kam (1987) Quarterly Reviews of Biophysics, 20, pp. 201–259]. The most common staining techniques are the May Grunwald Giemsa, Romanowsky-Giemsa, Hematoxylin-Eosin, Masson's trichrome and Papanicolaou staining. The Romanowsky-Giemsa staining procedure, for example, uses a combination of two dyes, one of which is Azure-B (trimethyl methionine), a thiazin dye, and the second being Eosin Y (hydroxyxanthene bromide). The thiazines are cationic dyes and therefore bind to acidic cellular constituents, whereas Eosin is an anionic dye and tends to bind to basic cellular constituents. It is widely accepted that the use of these two components creates the so-called Romanowsky-Giemsa effect, which is expressed as the development of a specific purple color, a new dye complex, in some stained sites. The molecular basis of the azure-B-Eosin complex is obscure. Some authors think that azure-B binds to anionic structures such as the phosphate groups of DNA, and that Eosin simultaneously binds both with an adjacent cationic site on the DNA and with the azure-B. In a more recently proposed model of the azure-B-Eosin complex, Friedrich and colleagues [Friedrich et al. (1990) Histochemistry 93, pp. 247–256] have suggested that azure-B first binds to phosphodiester residues of the DNA molecule. The authors have hypothesized that the phenyl group of the Eosin molecule is the portion that binds to the azure-B molecule (which lies in a single plane). The color purple is a result of a red shift of the Eosin absorption peak, which in turn is caused by the dielectric polarization of bound Eosin. The very existence of such an azure-B-Eosin complex is still questioned by others [see, Friedrich et al. (1990) Histochemistry 93, pp. 247–256; Bottiroli et al. (1994) Lasers in Surgery and Medicine; Profio (1984) IEEE Journal of Quantum Electronics QE-20 pp. 1502–1506; Herman (1989) Fluorescence Microscopy of Living Cells in Culture, part B, Chapter 8, pp. 219–243, edited by Taylor and Wang, Academic Press Inc.; and, Jovin and Amdt-Jovin (1989) Cell structure and function by microspectrofluorometry, Chapter 5, Academic Press Inc.].

Whatever the technique, with staining and/or chromogenic dying of cells and tissue sections it is possible to distinguish between subcellular compartments of the cell, and especially to distinguish the chromatin organization in the nucleus, proteins by means of tagged antibodies and genetic markers by means of labeled and hybridized probes. It is well established that the ratio between heterochromatin, stained dark blue, and euchromatin, stained pink, is one of the major determinants in the evaluation of cells in tissue sections. Also, it is well established that the simultaneous presence of certain combinations of proteins and genetic markers, and combinations of particular quantities, distributions and locations of same, are indicative of cancer type, grade, progression, and are used for diagnosis and prognosis. Similar applications of such technique are found in the detection, classification and diagnosis of infective diseases, due to bacteria, viruses of different types, and other pathogens. Nevertheless, the results obtained from stained specimens remain, to some degree, a matter of experience, art, and subjective interpretation. In order to diminish the effect of the scientist's experience, there have been attempts to study the spectroscopic characteristics of the interaction between organic stains and macromolecules, and thus to evaluate the so-called Romanowsky-Giemsa Effect of DNA staining. Spectral imaging applied to transmission light microscopy can greatly improve the quantitative measurement of size, shape and textural features of cell organs, cells and tissues. This technique is known as morphometry, which is a rapidly growing field in biology and pathology [Erler et al. (1993) Modern Pathology, 6, pp. 612–618]. As shown herein, morphometric spectral image (as opposed to simple morphometric image) analysis enables the evaluation of subtle cytological and histological features to yield useful ultrastructural and medical information for diagnostic and prognostic evaluation.

In some cases, spectral images acquired using transmission methods and unstained tissue may provide useful information, similar to that found in fluorescence microscopy techniques. One of the advantages of combining spectral bio-imaging and transmission microscopy without staining is the ability to use a "clean" measurement technique, i.e., no need for working with potentially toxic dyes or fixation agents.

Figure 15:
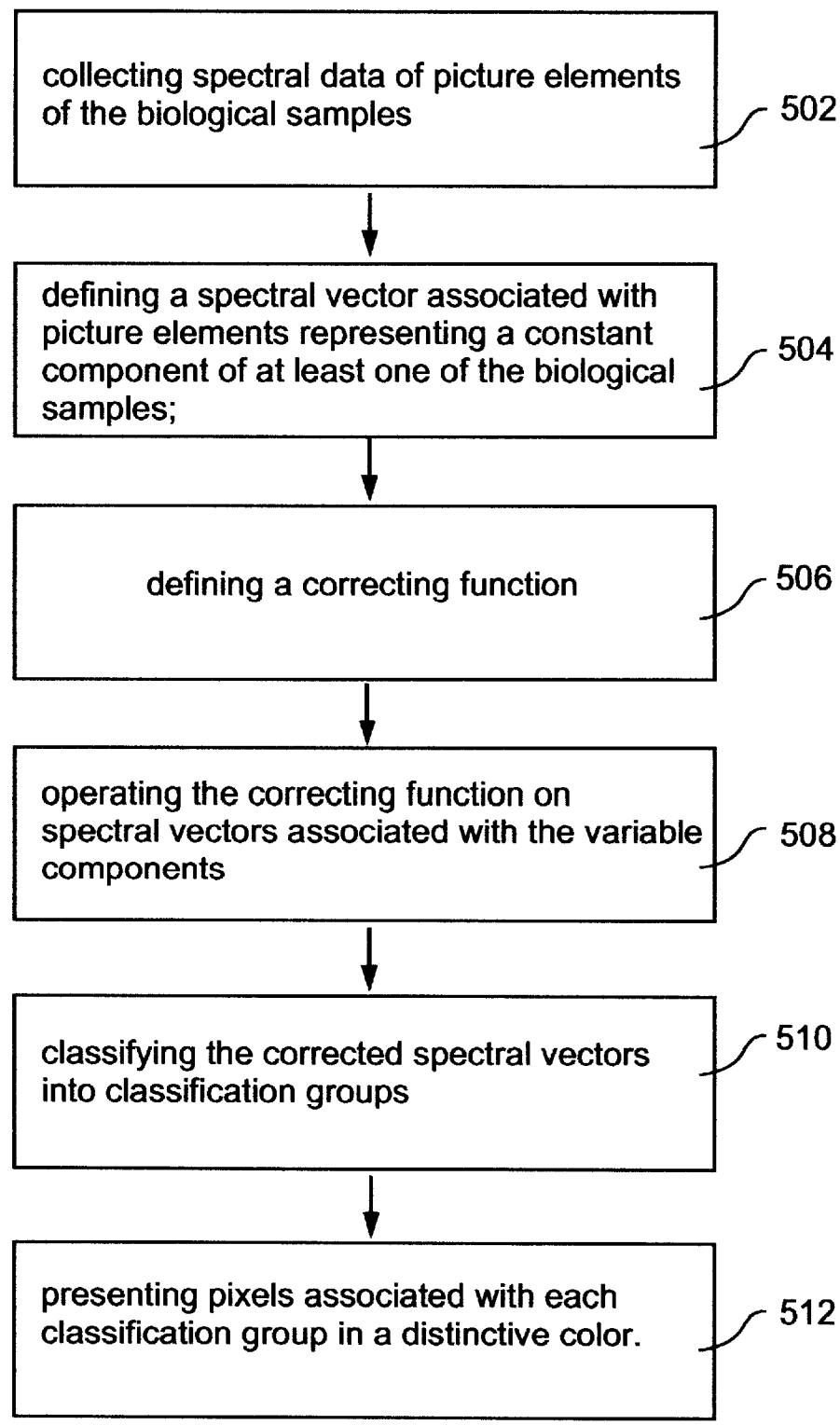
FIG. 15 is a flow chart diagram showing sequential steps of a method of spectral-morphometric analysis of biological samples according to the teachings of the present invention.

Thus, according to the present invention there is provided a method of spectral-morphometric analysis of biological samples which include substantially constant components and suspected variable components. As shown in FIG. 15 (steps 502–512), the method is effected by executing the following method steps, in which, in a first step a spectral data collection device is employed for collecting spectral data of picture elements of the biological samples. In a second step of the method, a spectral vector associated with picture elements representing a constant component of at least one of the biological samples is defined. In a third step of the method, that spectral vector is used for defining a correcting function which is selected such that when operated on spectral vectors associated with picture elements representing other constant components, the spectral vectors of the other constant components are modified to substantially resemble the above spectral vector. In a fourth step of the method the correcting function is operated on spectral vectors associated with at least the variable components for obtaining corrected spectral vectors thereof. Finally, the corrected spectral vectors are classified into classification groups.

The method according to the present invention preferably further includes a step in which pixels associated with each of the classification groups are presented in a distinctive color, e.g., on a display (monitor, computer screen, print, etc.).

The method according to the present invention is thus designed to provide modified spectral vectors of pixels associated with suspected variable components, which modified spectral vectors provide a better basis for classification by neutralizing variability of staining and/or instrumentation instability. Thus, the spectral vectors of the variable components are rendered independent of the measurement itself, and therefore allow for the building of spectral vector libraries and aid in the automatization of the analysis of the samples.

As used herein in the specification and in the claims section below, the term "spectral vector" refers to any type of spectral data, including, but not limited to, a spectrum. Also spectral data collected using, for example, a plurality (two or more) of specific band filters, e.g., narrow band filters, falls under this term.

As used herein in the specification and in the claims section below, the term "biological sample" refers to a sample retrieved from an animal, mammals and human beings in particular. The sample may be of a healthy tissue, disease tissue or tissue suspected of being disease tissue. The sample may be a biopsy taken, for example, during a surgical procedure. The sample may be collected via means of fine needle aspiration, scraping or washing a cavity to collects cells or tissue therefrom. The sample may be of a tumor both solid and hematopoietic tumors, as well as of neighboring healthy tissue. The sample may be a smear of individual cells or a tissue section.

As used herein in the specification and in the claims section below, the phrase "substantially constant components" refers to objects which should have the same spectrum when measured at different times under the same conditions, irrespective of the type of sample in which they are present. For example, red blood cells (RBC's) should have the same spectrum whether they are in a sample derived from a healthy person or from a leukemia patient, because it is assumed that their chemical composition does not change with the disease. Therefore, red blood cells are presently the preferred substantially constant components. In cases in which, for a reason or another, this assumption is not valid, inherently or substantially constant red blood cells derived from healthy blood or other constant biological material can be added to the sample to serve as the reference according to the present invention. In hematopoietic tumors red blood cells are inherently present in the examined samples. In solid tumors they are preferably added to at least a portion of the sample and otherwise they are used invariably as the reference material as described herein.

As used herein in the specification and in the claims section below, the phrase "suspected variable components" refers to objects which may have different characterizing spectra in patients of different diseases, as opposed to healthy individuals. According to an embodiment of the present invention, the suspected variable components are tumor cells, being analyzed for classification into tumor type and grade.

Thus, the method provided herein is basically a "calibration" or spectral "standardization" method, which allows a more meaningful comparison between different measurements by correcting out spectral shifts or distortions due to stain variability and/or instrumental instabilities.

Hematopoietic tumors according to the present invention include leukemias, lymphomas and other blood diseases, including, but not limited to, ALL, CLL, IM, PCL, PLL and Sezary syndrome.

Different stains bind different cellular constituents in different affinities, yet due to the presence of stain, a spectrum which is unique to each stained constituent is obtained. Suitable stains include but are not limited to Hematoxylin-Eosin staining and Giemsa staining or for some applications immunostaining [see, for example, Goto M, Nagatomo Y, Hasui K, Yamanaka H Murashima S and Sato E (1992) Chromaticity analysis of immunostained tumor specimens. Pathol. Res. Pract. 188:433]. However, it will be appreciated that for some applications cells which have not been stained are also suitable or preferred. This depends in part on lighting strategy and type of microscope employed, all as well known in the art.

Thus, according to a preferred embodiment of the present invention, prior to collecting spectral data of picture elements of the biological samples, the biological samples are stained, e.g., via immunohistochemical stain, a histological stain, a DNA ploidy stain, nucleic acid (DNA or RNA) sequence specific probes (from single locus, gene or EST sequence to whole chromosome or chromosomes paints) or any combination thereof. The histological stain can be, for example, Hematoxylin-Eosin stain, Giemsa stains of different types, Masson's trichrome or Papanicolaou stain.

These stains are presently widely used in tumor classification and grading as they differentially stain different classes and grades. Such stains can enhance the unique features of the tumor cells according to the present invention by attributing distinctive spectral signatures in a spatial dependent manner, resulting in improved spectral morphometry.

As used herein in the specification and in the claims section below, the term "stained" or "staining" refers to a process in which coloration is produced by foreign matter having penetrated into and/or interacted with the biological sample.

As used herein in the specification and in the claims section below, the term "stain" or "stains" refers to colorants, either fluorescent, luminescent and/or non-fluorescent (chromogenes) and further to reagents or matter used for effecting coloration.

As used herein in the specification and in the claims section below, the term "immunohistochemical stain" refers to colorants, reactions and associated reagents in which a primary antibody which binds a cytological marker is used to directly or indirectly (via "sandwich" reagents and/or an enzymatic reaction) stain the biological sample examined. Immunohistochemical stains are in many cases referred to in the scientific literature as immunostains, immunocytostains, immunohistopathological stains, etc.

As used herein in the specification and in the claims section below, the term "histological stain" refers to any colorant, reaction and/or associated reagents used to stain cells and tissues in association with cell components such as types of proteins (acidic, basic), DNA, RNA, lipids, cytoplasm components, nuclear components, membrane components, etc. Histological stains are in many cases referred to as counterstains, cytological stains, histopathological stains, etc.

As used herein in the specification and in the claims section below, the term "DNA ploidy stain" refers to stains which stoichiometrically bind to chromosome components, such as, but not limited to, DNA or histones. When an antibody is involved, such as anti-histone antibody, such stains are also known as DNA immunoploidy stains.

Lists of known stains are provided in U.S. patent application Ser. No. 09/122,704, filed Jul. 27, 1998, which is incorporated by reference as if fully set forth herein.

As used herein in the specification and in the claims section below, the phrase "nucleic acid sequence specific probe" refers to polynucleotides labeled with a label moiety which is either directly or indirectly detectable, which polynucleotides being capable of base-pairing with matching nucleic acid sequences present in the biological sample.

As used herein in the specification and in the claims section below, the term "spectral data collection device" refers to any device capable of detecting light intensity associated with a plurality, typically four or more, of distinct spectral bands in each spatial element (pixel) of the examined sample. For example, the SPECTRACUBE™ system optically connected to a microscope preferably serves as the spectral data collection device according to the present invention. However, any spectral imager, i.e., an instrument that measures and stores in memory for later retrieval and analysis the spectrum of light emitted by every point of an object which is placed in its field of view, including filters (e.g., conventional, acousto-optic tunable filter (AOTF) or liquid-crystal tunable filter (LCTF)) and dispersive element (e.g., grating or prism) based spectral imagers, or other spectral data or multi-band light collection devices (e.g., a device in accordance with the disclosure in Speicher R. M., Ballard S. G. and Ward C. D. (1996) Karyotyping human chromosomes by combinatorial multi-fluor FISH. Nature Genetics, 12:368–375) can be used to acquire the required spectral data. Also a device which includes a plurality of wide band filters, fixed, tunable, or built according to any mathematical definition, either based on decorrelation methods according to the procedures explained above and, for example, in U.S. Pat. No. 5,719,024, or others, or as described in U.S. patent application Ser. No. 08/917,213, filed Aug. 25, 1997, which is incorporated by reference as if fully set forth herein, can be used as the spectral data collection device according to the present invention. An additional possible type of spectral data collection device that can be used according to the present invention is one that is known in the literature as a "Step-scan infrared imaging system" sold by BioRad Laboratories Inc. of Cambridge Mass., USA, and described in: Fourier Transform Spectroscopic Imaging Using an Infrared Focal-Plane Array Detector, by E. Neil Lewis et al., Analytical Chemistry, Vol. 67, No. 19, Oct. 1, 1995, pp. 3377–3381, and histopathological applications of it are described in: Infrared Spectroscopic Imaging as a Tool for Pathology, by Linda H. Kidder et al., SPIE Proceedings Vol. No. 3257, Conference held in S. Jose Calif., USA, Jan. 24 to 30, 1998, and sold by BioRad Laboratories under the commercial name of Stingray 6000. It operates on unstained samples using IR light transmission, and it could be used with stained samples, if its optics were adapted for visible light. In such a system a commercial FT-IR step-scan interferometer is coupled to an IR microscope; samples mounted on quartz microscope slides are analyzed in transmission mode. The IR image is collected with a Cassegrain (reflective) objective. The image is projected to a liquid nitrogen-cooled InSb FPA (Focal Plane Array) detector (128×128 pixels) with a $CaF_2$ imaging lens. Of course, in this case the focal plane array should be replaced by a CCD or similar detector sensitive to visible light, the imaging lenses and other optics should be adapted to transmit and/or reflect visible light, and other system modifications should be introduced to make sure that the field, of view, spectral resolution, spatial resolution, measurement time, etc. are all reasonable and within feasible ranges. The interferometer timing and image acquisition are controlled externally via a computer. Therefore, it is intended not to limit the scope of the present invention for use of any specific type of spectral data collection device, nor to any specific type of spectral imager.

Thus, the spectral data collection device can be an interferometer-based spectral data collection device of any kind, filter(s)-based spectral data collection device and a dispersion element-based spectral data collection device.

According to a preferred embodiment of the present invention, collecting spectral data of picture elements of the biological samples is effected by (i) collecting incident light simultaneously from all pixels of the sample using collimating optics; (ii) passing the incident collimated light through an interferometer system having a number of elements, so that the light is first split into two coherent beams which travel in different directions inside the interferometer and then the two coherent beams recombine to interfere with each other to form an exiting light beam; (iii) passing the exiting light beam through a focusing optical system which focuses the exiting light beam on a detector having a two-dimensional array of detector elements, so that at each instant each of the detector elements is the image of one and always the same pixel of the sample for the entire duration of the measurement, so that the real image of the sample is stationary on the plane of the detector array and at any time during the measurement the image is still visible and recognizable, and so that each of the detector elements produces a signal which is a particular linear combination of light intensity emitted by the pixel at different wavelengths, wherein the linear combination is a function of the instantaneous optical path difference; (iv) scanning one or more of the elements of the interferometer system, so that the optical path difference between the two coherent beams generated by the interferometer system is scanned simultaneously for all the pixels of the sample; and (v) recording signals of each of the detector elements as function of time using a recording device to form a spectral cube of data.

According to a preferred embodiment of the present invention classifying the corrected spectral vectors into classification groups is effected using a classification map algorithm which employs reference spectral vectors for associating picture elements into the classification groups. The reference spectral vectors used for classification can be derived from a previously prepared reference spectral vectors library. According to a preferred embodiment of the present invention at least one of the reference spectral vectors for classification is of picture element(s) derived from a cell domain selected from the group consisting of nucleolus, inter-chromosomal region, cytoplasm, a first chromatin region of the nucleus, a second chromatin region of the nucleus and background. Classification can alternatively be effected by spectral maxima classification, as further exemplified in the Examples section below.

Each of the various embodiments and aspects of the present invention as delineated hereinabove and as claimed in the claims section below finds experimental support in the Examples section that follows.

EXAMPLES

Reference in now made to the following examples, which together with the above descriptions, illustrate the invention.

Materials and Methods

May Grunwald Giemsa (MGG) Staining of Peripheral Blood Specimens

Peripheral blood was obtained from normal healthy individuals and from patients with typical acute lymphocytic leukemia (ALL), chronic lymphocytic leukemia (CLL), infectious mononucleosis (IM), plasma cell lymphoma (PCL), prolymphocytic leukemia (PLL) and Sezary syndrome (SEZARY), which were diagnosed according to established criteria. The patients did not receive chemotherapy for at least 3 months before obtaining the samples.

Fourier-Transform Multipixel Spectrometry System for Microscopy

The SPECTRACUBE™ system (Applied Spectral Imaging (ASI) Ltd., Industrial Park, Migdal Haemek, Israel) was used for spectral imaging of the samples. The SPECTRACUBE™ system employed includes a Sagnac interferometer which is a particular type of triangular interferometer (see FIG. 3 above) and has high mechanical and thermal stability. The light beam passing through the specimen is split in the interferometer in different directions, and is united again at the exit with an optical path difference (OPD) which is a function of the angle (θ) between the incoming beam and the optical axis of the interferometer itself. The OPD arises because for non-zero angles the two beams undergo different optical paths in the beamsplitter. The inherent mechanical stability of this interferometer allows the Fourier technique to be successfully applied to the visible spectral region. Wavelength calibration is performed by measuring a series of known monochromatic sources and then building a quadratic best-fit table of the wavelength versus "channel" parameter, the independent variable proportional to $1/\lambda$ (resulting from the fast Fourier transform, FFT). The interferometer forms interference fringes at infinity, so that they show up on the CCD focal plane as lines of intensity modulation superimposed on the image of the sample. The actual measurement is done by recording successive CCD frames in synchronization with the steps of the motor used to rotate the collimated beam, so that the instantaneous OPD is known for every pixel in every recorded frame and can be used in the FFT calculation. During a measurement, each detector element of the CCD (512×512, in this case) is collecting an interferogram, which is then Fourier transformed to give the spectrum of the corresponding pixel. The spectral and spatial resolutions, spectral range and other characteristics of the system employed are summarized in Table 1, above.

Spectral Classification Analysis

Spectral correction or standardization, using the spectrum of pixels associated with red blood cells, as further detailed hereinbelow was used prior to classification to enhance thereafter spectral features and to correct for spectral differences associated with e.g., sample preparation, source, etc. This latter procedure, in effect, is the gist of the present invention.

Modeling and Description of the Method

To model and describe the method of the present invention, consider the following definitions and procedures.

Define the spectrum of the substantially constant component (red blood cells averaged, for example, over 5 pixels in the examples used in this specifications) taken from one of the spectral image measurements, as $SR(\lambda)$, where λ is the wavelength. Consider also the spectrum of the substantially constant component taken from another spectral image measurement, or a second measurement, for the purposes of this explanation, be it $SRBC(\lambda)$.

Define for each of the above measurements respectively:

$IR(\lambda)$, $I(\lambda)$: spectral intensity functions of the illumination on the sample;

CR, C: attenuation constants independent of wavelength and of pixel position, which may be due to dirt on the optics or any other cause;

$KR(\lambda)$, $K(\lambda)$: spectral response functions of the measurement system including the spectral transmission of the optics and the spectral response function of the detector array;

$SMR(\lambda)$, $SM(\lambda)$: measured spectra of the same type of object M in the two different measurements (it could be cytoplasm, heterochromatin, euchromatin, an organelle, a stained protein by immunological labeling, a stained DNA section or gene, etc.)

$DR(\lambda)$, $D(\lambda)$, $DMR(\lambda)$, $DM(\lambda)$: spectral transmission due to staining variability from measurement to measurement and from object to object. $DR(\lambda)$ and $D(\lambda)$ correspond to the RBC's of the reference and the second measurement respectively, $DMR(\lambda)$ and $DM(\lambda)$ correspond to the object, M, measured respectively in the reference and in the second measurement.

One can then write:

$$SR(\lambda)=CR\ IR(\lambda)DR(\lambda)KR(\lambda),$$

One can also write:

$$SRBC(\lambda)=C\ I(\lambda)D(\lambda)K(\lambda)$$

$$SMR(\lambda)=CR\ IR(\lambda)DMR(\lambda)KR(\lambda)$$

and $$SM(\lambda)=C\ I(\lambda)DM(\lambda)K(\lambda).$$

Define now the correction function for the second measurement, under the assumption that the illumination functions $I(\lambda)$ and $IR(\lambda)$, and the spectral response functions of the measurement system $K(\lambda)$ and $KR(\lambda)$ are not dependent on the pixel position within each measurement:

$$X(\lambda) = \frac{S_R(\lambda)}{S_{RBC}(\lambda)} = \frac{C_R I_R(\lambda) D_R(\lambda) K_R(\lambda)}{C I(\lambda) D(\lambda) K(\lambda)}$$

The above assumption is needed because $X(\lambda)$, which is a function of I, IR, K and KR, is built from one region of the image, and used to correct spectra in another region of the image.

The next step is to build a new spectral image by multiplying the correction function $X(\lambda)$ by the spectrum of each pixel of the second measurement. The resulting spectrum of an RBC cell will be:

$$\overline{S}_{RBC}(\lambda)=X(\lambda)S_{RBC}(\lambda)=S_R(\lambda)$$

which is true by definition of $X(\lambda)$.

The resulting corrected spectrum of the object M will be:

$$\overline{S}_M(\lambda) = X(\lambda)S_M(\lambda) =$$

$$\frac{C_R I_R(\lambda) D_R(\lambda) K_R(\lambda)}{C I(\lambda) D(\lambda) K(\lambda)} C I(\lambda) D_M(\lambda) K(\lambda) = \frac{C_R I_R(\lambda) D_R(\lambda) K_R(\lambda)}{D(\lambda)} D_M(\lambda)$$

Now assume that $DR(\lambda)$, $D(\lambda)$, $DMR(\lambda)$, $DM(\lambda)$ are related by a distortion variability function $Y(\lambda)$ as follows:

$$D(\lambda)=D_R(\lambda)Y(\lambda)$$

and $$D_M(\lambda)=D_{MR}(\lambda)Y(\lambda)$$

This assumption means that the spectral distortion due to variability of staining can be expressed by a function $Y(\lambda)$, which is specific of a spectral image measurement and is common to all the pixels of the measurement. Under this assumption we obtain, by eliminating $Y(\lambda)$ from the last two equations:

$$\frac{D_M(\lambda)D_R(\lambda)}{D(\lambda)} = D_{MR}(\lambda)$$

and substituting this last relation into the expression for $\overline{S}_M(\lambda)$ we obtain:

$$\overline{S}_M(\lambda)=C_R I_R(\lambda)D_{MR}(\lambda)K_R(\lambda)=S_{MR}(\lambda)$$

This last relation means that the corrected spectrum of object M in the spectral image of the second measurement is equal to the spectrum of the same type of object as appearing in the spectral image of the reference measurement. The validity of the assumption of constancy of the function Y(λ) over a spectral image can be checked in a practical measurement of controlled and known cells or tissue, by comparing similar types of cells from the same patient in different measurements, before and after the correction.

Figure 11:
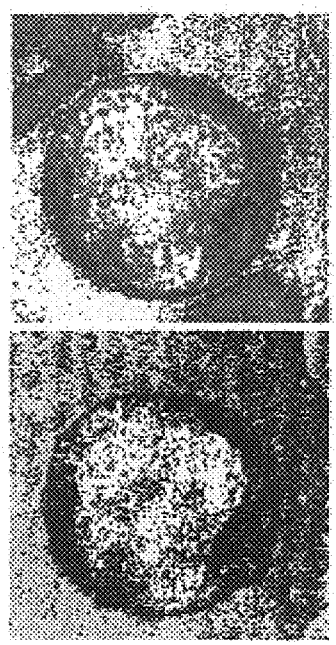
Figure 11:
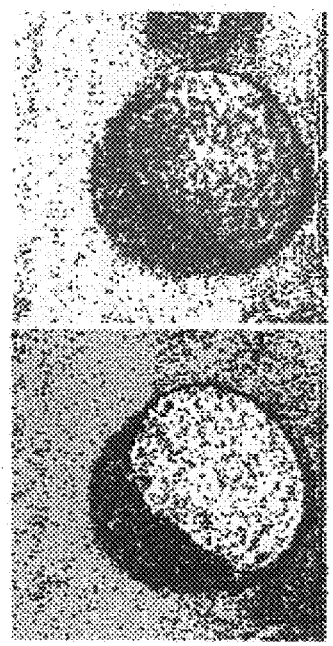
Figure 12:
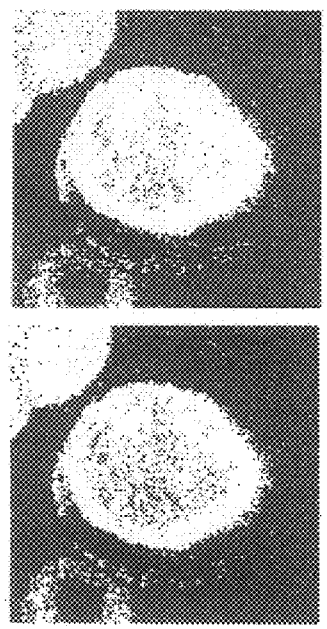
Figure 12:
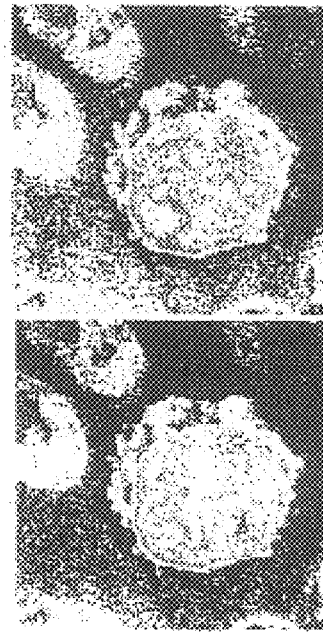
Figure 13:
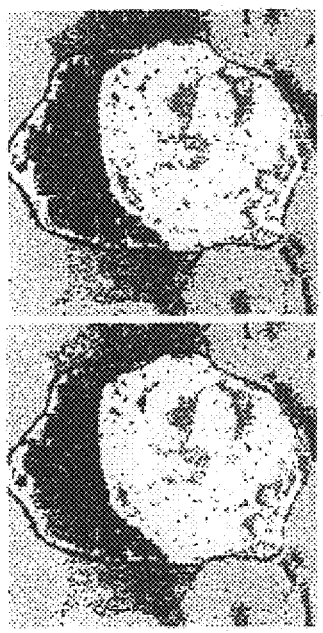
Figure 14:
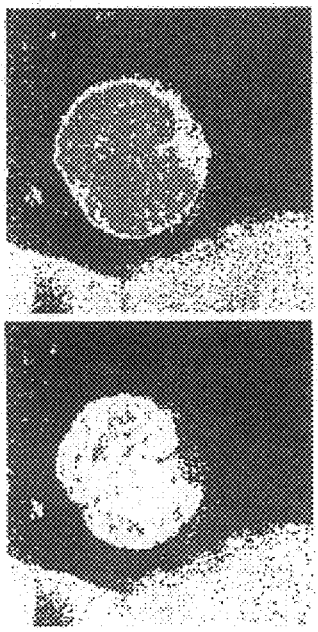
Figure 14:
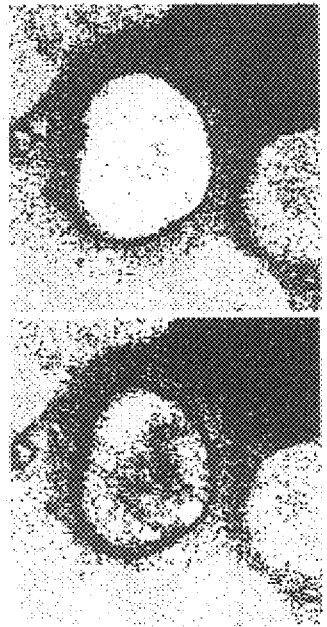

FIG. 11, for example, shows that this is a reasonable assumption: for example, all cells measured in IM10, IM11, PLL24, and SEZARY20 spectral images, while looking very different from the corresponding cells of the same disease of different patients before the correction, they show a very similar pixel classification after the correction method explained above has been applied to them.

Experimental Results

Figure 5:
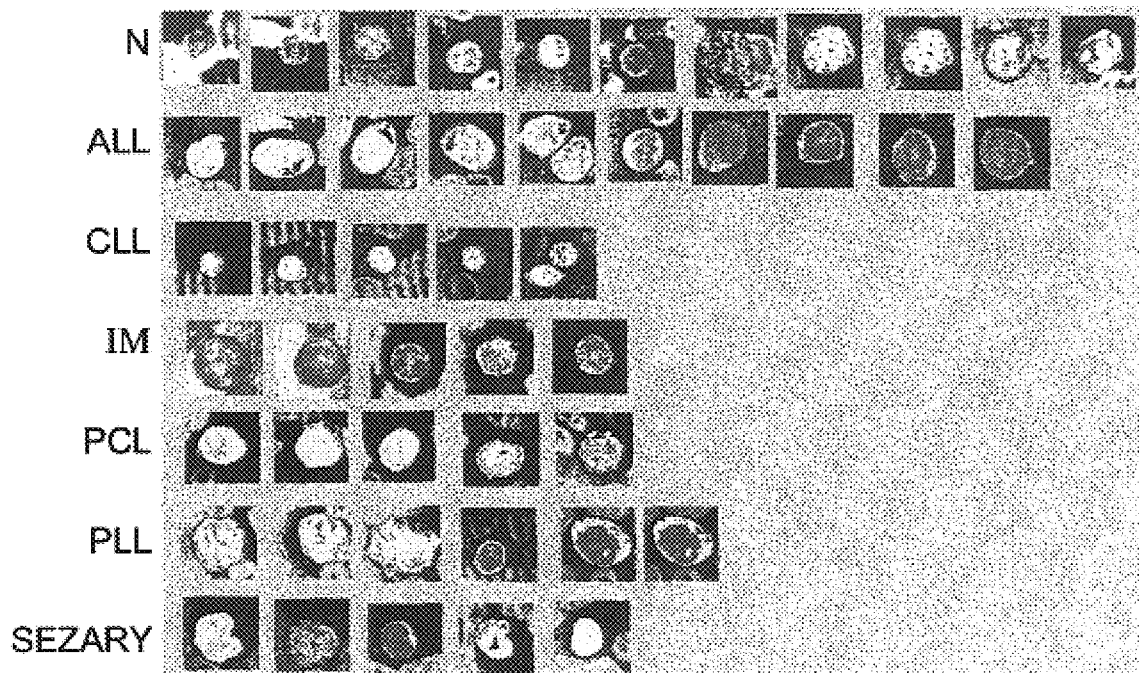
FIG. 5 presents leukemia cells classified using the SPECTRACUBE™ system. The classification technique employed was based on pixel's spectrum classification according to the wavelength at which the spectrum is maximum. Classification colors are according to the definitions of Table 2 below. The black color stands for both background pixels, and pixels which remained unclassified because their spectrum was too different from any of the other classes. Peripheral blood samples were from normal healthy individuals (N) and from patients with typical acute lymphocytic leukemia (ALL), chronic lymphocytic leukemia (CLL), infectious mononucleosis (IM), plasma cell lymphoma (PCL), prolymphocytic leukemia (PLL) and Sezary syndrome (SEZARY), which were diagnosed according to established criteria.

FIG. 5 presents leukemia cells classification using the SPECTRACUBE™ system, before any correction was applied. The classification technique employed was based on pixel's spectrum classification according to the spectral band in which the spectrum maximum occurs as follows. First, a spectral image (spectral cube) was measured. Second, the cube was normalized, i.e., stretched to a full dynamic range (0–1), by dividing it by a constant equal to the maximum signal present in the cube. Then, based on spectral maxima, each pixel was assigned a specific artificial color, according to the definition of Table 2 below. Table 2 below associates spectral bands of spectral maxima with classification colors. A total of nine classification groups were used: 8 for different cell features, and one, black, for all the pixels which are either background or are not classified in any of the other 8 groups. Similar results were obtained using a conventional classification approach as described hereinabove.

TABLE 2

| Spectral Maxima Range (nm) | Artificial Color |
| --- | --- |
| 700.6–712.6 | Blue |
| 678.2–689.2 | White |
| 657.3–667.5 | Red |
| 637.9–647.4 | Cyan |
| 619.8–628.7 | Yellow |
| 602.9–611.2 | Black |
| 587.1–594.9 | Gray |
| 572.2–579.5 | Magenta |

Viewing the classification results shown in FIG. 5, one observes that some differences between cells derived from the normal individual (N) and cells derived from each of the various patients (ALL, CLL, IM, PCL, PLL and SEZARY) are apparent. To a lesser extent, differences among cells within each group are observed as well.

For each of the individuals studies, in addition to the nucleated cells, anucleated, red blood cell (RBC), which are not related to the disease are apparent. However, in some of the cases spectra associated with RBC's are variable. Compare, for example, the two left images of the IM group as compared to the other three images in the same group, or the fifth image in the PLL group as compared to the others. These variations raised the question whether the staining and measuring technique are stable enough and invariant to provide reproducible and indicative results.

In order to overcome possible variations between different cubes a correction technique is needed.

Such a technique, which is the gist of the present invention, is based on the stipulation that the properties of the red blood cell are inherently invariant, so that their spectrum should be invariant as well, and that a spectral change or shift due to differential staining affects the RBC's and the rest of the sample in a similar way.

Figure 6:
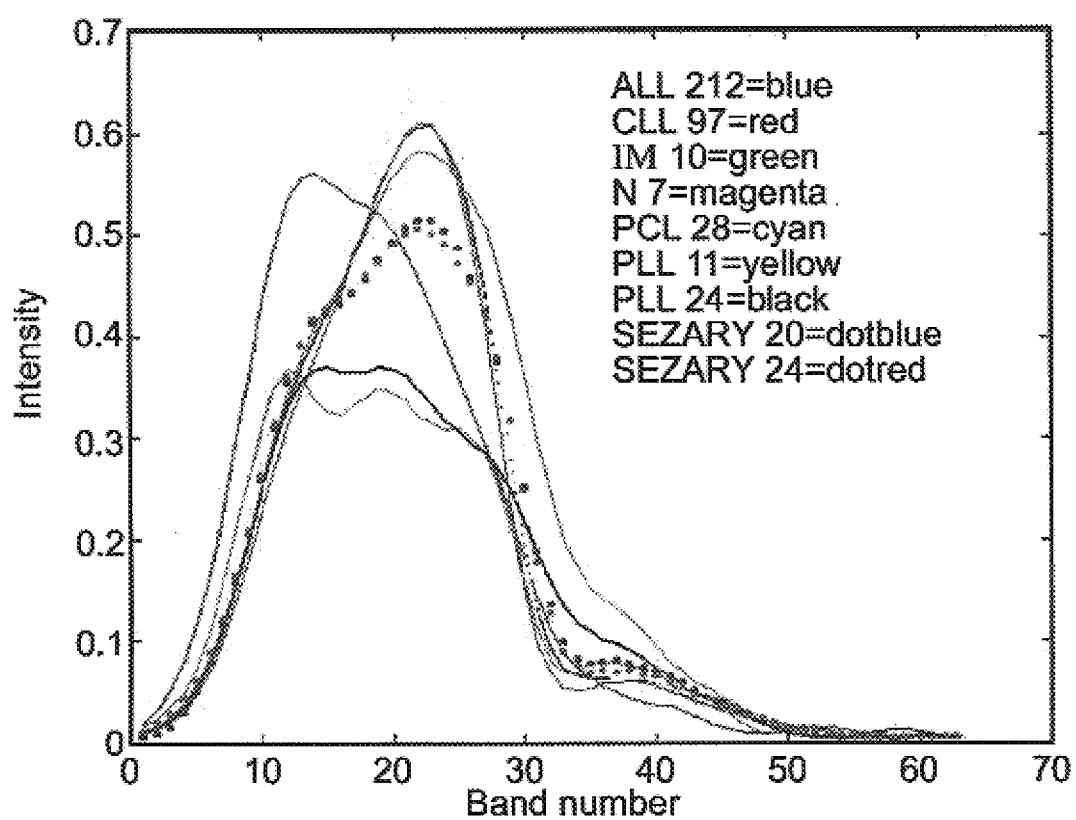
FIG. 6 presents variations among red blood cells (RBC's) spectra from various patients ALL212, CLL97, IM10, N7, PCL28, PLL11, PLL24, SEZARY20 and SEZARY24, wherein the numbers indicate a specific patient of the specified disease.

The variations among RBC's spectra from various patients were checked by constructing a mean spectrum (five pixel mean) of a red blood cell in each cube. These spectra are shown in FIG. 6, for the following cubes, ALL212, CLL97, IM10, N7, PCL28, PLL11, PLL24, SEZARY20 and SEZARY24, wherein the numbers after the acronym of each type of disease indicate a specific patient affected by that specific disease. These cubes were chosen because each of them contains at least one well defined blood cell, which can be used to demonstrate the invention.

One clearly observes that, indeed, there are spectral variations among cubes, wherein, in the example given, the RBC's of ALL212, PCL28 and PLL11 have similar spectra, CLL97's is slightly different, SEZARY20 and SEZARY24's show a larger difference but are still very similar to each other, N7 and PLL24 do differ but are very close to each other and the green curve IM10 shows a vastly different spectrum.

The spectral standardization procedure according to the present invention as described hereinabove was carried out for the nine cubes under discussion (ALL212, CLL97, IM10, N7, PCL28, PLL11, PLL24, SEZARY20 and to SEZARY24). After the spectral correction was performed, the corrected cubes were classified, using the same procedure as described with respect to FIG. 5.

Figure 7:
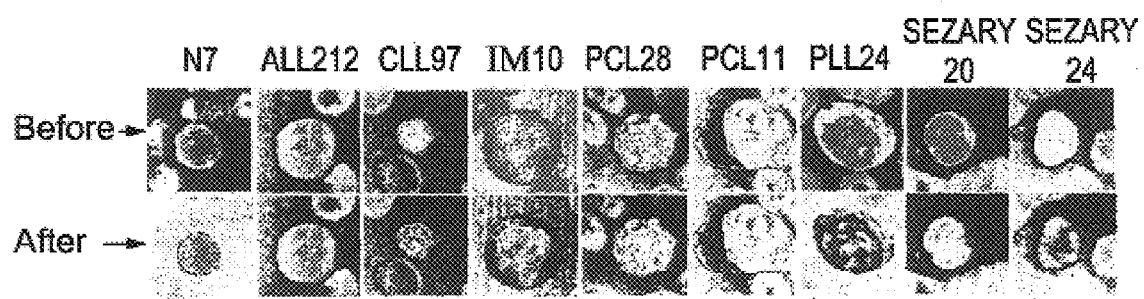
FIG. 7 presents cells derived from the various patients listed in FIG. 6 before (upper row) and after (lower row) modification using the correcting algorithm according to the present invention.
Figure 8:
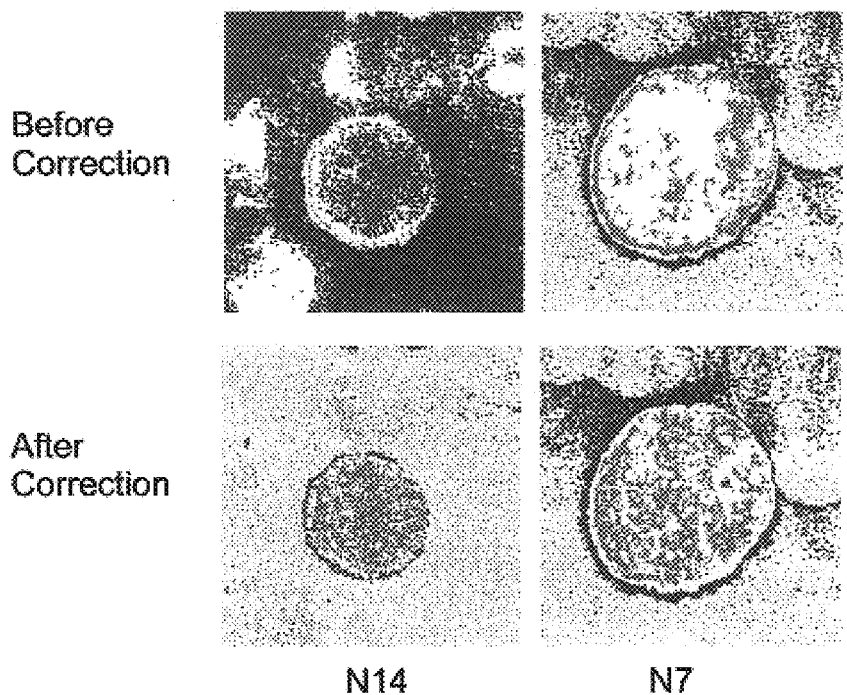
FIGS. 8–14 show before and after correction results from various patients of the Normal, ALL, CLL, IM, PCL, PLL and SEZARY groups. Please note the identity of the RBC's after correction, among all measurements, and the similar appearance of the cells after correction within each group and among the different groups.
Figure 9:
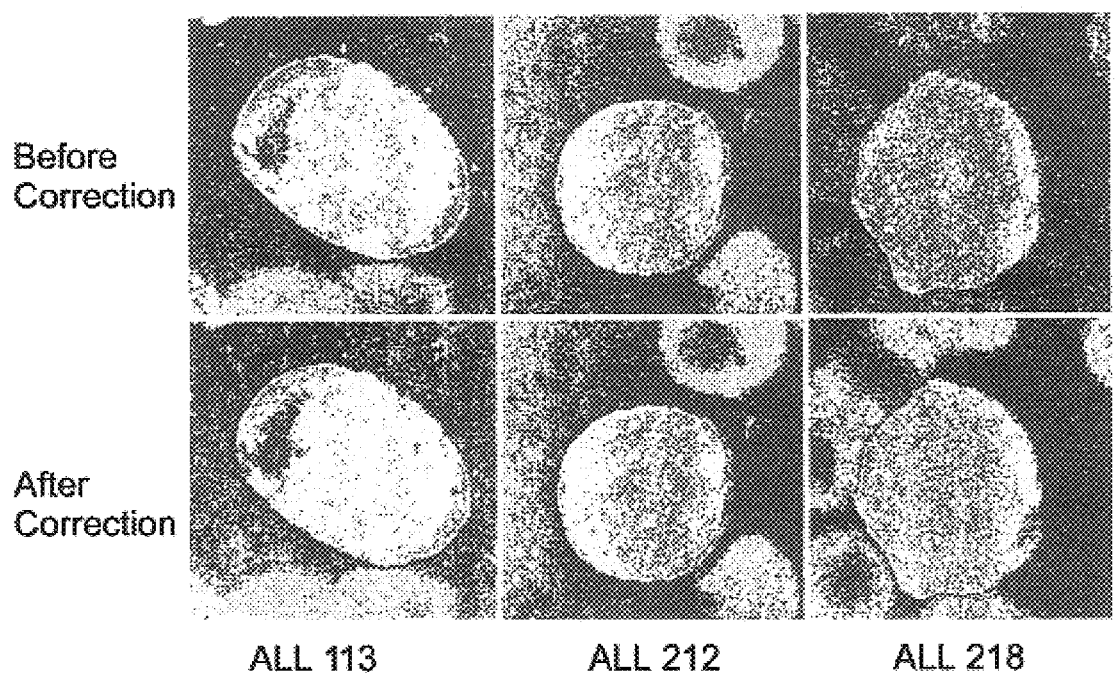
Figure 10:
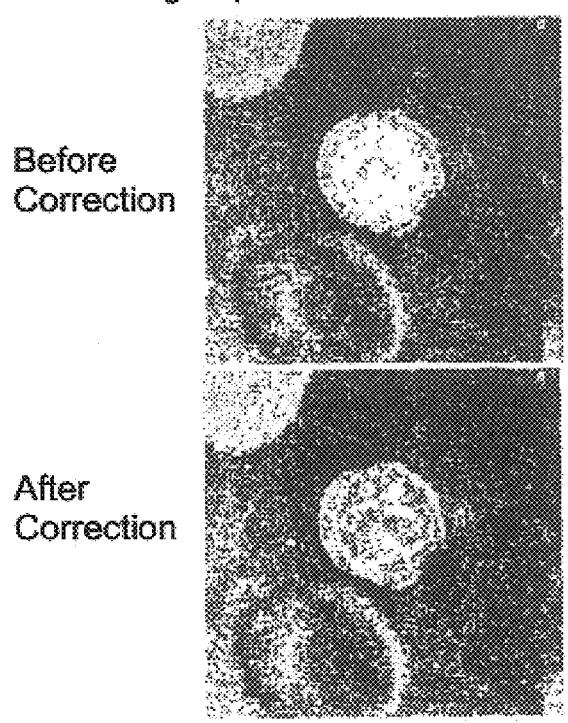

The classification results, before and after modification using the above standardization algorithm are shown in FIG. 7, where the upper row shows the classification results before correction and the bottom row after correction.

One observes that, obviously, the ALL212 cube did not change at all since by definition, the correcting function for this cube is equal to 1 for all wavelengths, as easily seen from the equation defining the correcting function when substituting SR(λ) for SRBC(λ). The areas outside the nucleus, which should be invariant are indeed so. The most significant change occurred in the IM10 cube because the RBC spectrum in this cube is most different from the RBC spectrum of the ALL212 cube; now the corrected IM10 cube resembles much more the other IM cubes (see FIG. 5), as expected. The two PLL and SEZARY cubes which vastly differ from one another prior to correction, are now similar to each other.

These results indicate that this or a similar correction procedure may indeed aid to achieve a more meaningful comparison between different bright field measurements of stained cells or tissue sections, performed in different days and/or in different laboratories. Consequently, group identification should be performed using the corrected cubes and not the raw cubes.

FIGS. 8–14 show results from various patients of the Normal, ALL, CLL, IM, PCL, PLL and SEZARY groups before and after correction. Please note the homogeneous appearance of the cells after correction in all groups and among groups.

Thus, the following conclusions can be drawn from the above results. First, the variations inside groups are removed after normalization. Second, the spectral differences between most groups are very small. The spectra of the nucleus is vastly different than the red blood cells and the surrounding material.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A method of spectral-morphometric analysis of biological samples, the biological samples including substantially constant components and suspected variable components, the method comprising the steps of:
   (a) using a spectral data collection device for collecting spectral data of picture elements of the biological samples;
   (b) defining a spectral vector associated with picture elements representing a constant component of at least one of the biological samples;
   (c) using said spectral vector for defining a correcting function being selected such that when operated on spectral vectors associated with picture elements representing other constant components, spectral vectors of said other constant components are modified to substantially resemble said spectral vector;
   (d) operating said correcting function on spectral vectors associated with at least said variable components for obtaining corrected spectral vectors thereof; and
   (e) classifying said corrected spectral vectors into classification groups.

2. The method of claim 1, further comprising the step of:
   (f) presenting pixels associated with each of said classification groups in a distinctive color.

3. The method of claim 1, wherein the substantially constant components are red blood cells.

4. The method of claim 3, wherein said red blood cells are added to the biological sample.

5. The method of claim 3, wherein said red blood cells are inherent to the biological sample.

6. The method of claim 1, wherein said suspected variable components are tumor cells, tumor tissues or parts thereof.

7. The method of claim 6, wherein said tumor cells are hematopoietic tumor cells.

8. The method of claim 6, wherein the substantially constant components are red blood cells.

9. The method of claim 1, wherein said biological sample is a blood sample of a patient suspected to have or having a hematopoietic tumor.

10. The method of claim 9, wherein said hematopoietic tumor is selected from the group consisting of leukemia and lymphoma.

11. The method of claim 1, wherein said biological sample is of a patient suspected of having or having a disease selected from the group consisting of ALL, CLL, IM, PCL, PLL and Sezary syndrome.

12. The method of claim 1, wherein prior to collecting spectral data of picture elements of the biological samples, the biological sample is stained.

13. The method of claim 12, wherein staining said biological sample is effected via a stain selected from the group consisting of an immunohistochemical stain, a histological stain, a DNA ploidy stain, a nucleic acid sequence specific probe and any combination thereof.

14. The method of claim 13, wherein said histological stain is selected from the group consisting of Hematoxylin-Eosin stain, May Grunwald Giemsa stain, Romanowsky Giemsa stain, Masson's trichrome stain and Papanicolaou stain.

15. The method of claim 1, wherein collecting spectral data of picture elements of the biological samples is effected by:
   (i) collecting incident light simultaneously from all pixels of said sample using collimating optics;
   (ii) passing said incident collimated light through an interferometer system having a number of elements, so that said light is first split into two coherent beams which travel in different directions inside said interferometer and then said two coherent beams recombine to interfere with each other to form an exiting light beam;
   (iii) passing said exiting light beam through a focusing optical system which focuses said exiting light beam on a detector having a two-dimensional array of detector elements, so that at each instant each of said detector elements is the image of one and always the same pixel of said sample for the entire duration of the measurement, so that the real image of the sample is stationary on the plane of the detector array and at any time during the measurement the image is still visible and recognizable, and so that each of said detector elements produces a signal which is a particular linear combination of light intensity emitted by said pixel at different wavelengths, wherein said linear combination is- a function of the instantaneous optical path difference;
   (iv) scanning one or more of said elements of said interferometer system, so that said optical path difference between said two coherent beams generated by said interferometer system is scanned simultaneously for all said pixels of said sample; and
   (v) recording signals of each of said detector elements as function of time using a recording device to form a spectral cube of data.

16. The method of claim 1, wherein said spectral data collection device includes an element selected from the group consisting of a dispersion element, a filter and an interferometer.

17. The method of claim 1, wherein classifying said corrected spectral vectors into classification groups is effected using a classification map algorithm which employs reference spectral vectors for associating picture elements into said classification groups.

18. The method of claim 17, wherein said reference spectral vectors for classification are of a previously prepared reference library.

19. The method of claim 17, wherein at least one of said reference spectral vectors for classification is of picture elements derived from a cell domain selected from the group consisting of nucleolus, inter-chromosomal region, cytoplasm, a first chromatin region of the nucleus, a second chromatin region of the nucleus and background.

20. The method of claim 1, wherein said spectral vector is a normalized spectral vector.

21. The method of claim 1, wherein classifying said corrected spectral vectors into classification groups effected by spectral vector maxima classification.

22. The method of claim 1, wherein said suspected variable components are cells infected by a pathogen.

* * * * *